(12) United States Patent
Murphy

(10) Patent No.: US 7,468,269 B2
(45) Date of Patent: Dec. 23, 2008

(54) REAGENTS FOR RECOMBINOGENIC ENGINEERING AND USES THEREOF

(75) Inventor: Kenan C. Murphy, Natick, MA (US)

(73) Assignee: University of Massachusetts, Boston, MA (US)

(*) Notice: Subject to any disclaimer, the term of this patent is extended or adjusted under 35 U.S.C. 154(b) by 258 days.

(21) Appl. No.: 10/789,186

(22) Filed: Feb. 26, 2004

(65) Prior Publication Data

US 2005/0048470 A1 Mar. 3, 2005

Related U.S. Application Data

(60) Provisional application No. 60/450,474, filed on Feb. 26, 2003.

(51) Int. Cl.
*C12N 1/21* (2006.01)
(52) U.S. Cl. .............................. 435/252.33; 435/252.34; 435/252.3
(58) Field of Classification Search ............... 435/320.1
See application file for complete search history.

(56) References Cited

U.S. PATENT DOCUMENTS

| 4,363,877 | A | 12/1982 | Goodman et al. | |
|---|---|---|---|---|
| 6,355,412 | B1* | 3/2002 | Stewart et al. | 435/4 |
| 6,783,930 | B1* | 8/2004 | Pelletier et al. | 435/5 |

OTHER PUBLICATIONS

Poteete, A.R. and Fenton, A.C. Genetic Requirements of Phage Lambda Red-Mediated Gene Replacement in *Escherichia coli* K-12, Journal of Bacteriology 182(8):2336-2340, 2000.*
Datsenko, K.A. and Wanner, B.L. One-step Inactivation of Chromosomal Genes in *Escherichia coli* K-12 using PCR Products, PNAS 97(12):6640-6645, 2000.*
Murphy, K.C. Biochemical Characterization of P22 Phage-modified *Escherichia coli* RecBCD Enzyme. The Journal of Biological Chemistry 269(36):22507-22516, 1994.*
Groth, A. and Calos, M. Phage Integrases: Biology and Applications. Journal of Molecular Biology 335:667-678, 2004.*
Poteete, A.R. et al. Roles of RuvC and RecG in Phage Lambda Red-Mediated Recombination. Journal of Bacteriology 181(17):5402-5408, 1999.*
Cookson, Brad T. et al, "Mutagenesis of *Bordetella pertussis* with Transposon Tn5tac1: Conditional Expression of Virulence-Associated Genes," *Journal of Bacteriology*, vol. 172(4):1681-1687 (1990).
DeVito, Joseph A. et al, "An array of target-specific screening strains for antibacterial discovery," *Nature Biotechnology*, vol. 20:478-483 (2002).
Kong, Deyu et al, "Whole-virus Vaccine Development by Continuous Culture on a Complementing Host," *Bio/Technology*, vol. 13:583-586 (1995).
Poteete, Anthony R., "What makes the bacteriophage λ Red system useful for genetic engineering: molecular mechanism and biological function," *FEMS Microbiology*, vol. 201:9-14 (2001).
International Search Report Application No. PCT/US04/05992, dated Nov. 28, 2005.

* cited by examiner

*Primary Examiner*—Nancy Vogel
(74) *Attorney, Agent, or Firm*—Lahive & Cockfield, LLP; Debra J. Milasincic, Esq.; Megan E. Williams, Esq.

(57) ABSTRACT

The present invention features homologous recombination methods and systems. The methods and systems promote highly efficient homologous recombination in cells (e.g., in prokaryotic cells). The methods and systems are useful, for example, in pharmaceutical drug development, vaccine development and cloning.

11 Claims, 7 Drawing Sheets

A. λ Red recombination with plasmid substrates

B. λ Red recombination with PCR substrates

Tir-PPP  Tir-PHP  Tir-HHH$_{NBS}$

Plasmid Expression

Tir-PPP   Tir-PHP   Tir-HHH$_{NBS}$

Chromosomal Expression

Tir-PPP        Tir-PHP        Tir-HHH$_{NBS}$

REAGENTS FOR RECOMBINOGENIC ENGINEERING AND USES THEREOF

RELATED APPLICATIONS

This application claims the benefit of U.S. Provisional patent application Ser. No. 60/450,474, entitled "Improved Reagents for Recombinogenic Engineering and Uses Thereof", filed Feb. 26, 2003 (pending). The entire content of the above-referenced patent application is hereby incorporated by this reference.

GOVERNMENT RIGHTS

This invention was made at least in part with government support under grant no. R21-GM62482 awarded by the National Institutes of Health. The government may have certain rights in this invention.

BACKGROUND OF THE INVENTION

A new method for engineering bacterial chromosomes has emerged in recent years that takes advantage of the high proficiency of bacteriophage recombination systems acting on linear DNA substrates (for review, see Court et al., 2002). The λ Red recombination system, consisting of Bet (a ssDNA annealing protein) and Exo (a 5'-3' dsDNA exonuclease) promotes gene replacement of electroporated linear DNA substrates into the *Escherichia coli* K-12 chromosome at a very high efficiency (Murphy, 1998; Murphy et al., 2000). Inactivation of host RecBCD exonuclease activity, either by mutation or production of the anti-RecBCD λ Gam function, is required for efficient Red-promoted recombination with linear dsDNA substrates (Murphy, 1998). Zhang and co-workers (Zhang et al., 1998), using the *E. coli* rac prophage RecET recombination system, recognized that PCR-generated substrates with as little as 40 bp of homology could serve as efficient substrates for gene replacement in *E. coli*. The use of such substrates has also been demonstrated with the λ Red system, with Red and Gam being supplied from either a prophage (Yu et al., 2000), a low-copy number plasmid (Datsenko and Wanner, 2000), or from a ΔrecBCD::Ptac-gam-red chromosomal substitution (Murphy, 1998; unpublished observations). The high efficiency of Red and RecET-promoted recombination with such short regions of homology has allowed *E. coli* geneticists to perform oligo-directed gene replacements that yeast geneticists have performed for years (Baudin et al., 1993; Lorenz et al., 1995; Wach et al., 1994).

SUMMARY OF THE INVENTION

The present invention features improved methods and systems for promoting recombination in bacteria. In particular, the invention features an improved λ Red recombination system. This improved system is particularly suited for recombination in pathogenic strains of bacteria.

The present invention provides isolated nucleic acid molecules and vectors encoding bacteriophage recombinases, e.g., bacteriophage λ Red and Gam, which are operably linked to a promoter, e.g., Ptac promoter, and the LacI repressor. The bacteriophage recombinases promote homologous recombination between nucleic acid material. Preferably the vectors of the invention further consist of a temperature-sensitive origin of replication that confers low copy number upon the vector.

The present invention also features recombinant organisms, e.g., bacteria or pathogenic bacteria, which contain vectors of the present invention and methods of using the recombinant organisms to promote efficient recombination of genetic material. The genetic material undergoing recombination can be endogenous or exogenous, and can be derived from a prokaryote or a eukaryote.

The present invention further provides methods of identifying potential drug targets in a recombinant microorganism of the invention, e.g., a pathogenic bacterium, by promoting recombination between a gene of the microorganism and an integrating segment introduced by a test construct. Preferably the integrating segment encodes a selectable marker.

The present invention also provides methods of producing vaccines and vaccine antigens.

Other features and advantages of the invention will be apparent from the following detailed description and claims.

Figure 1:
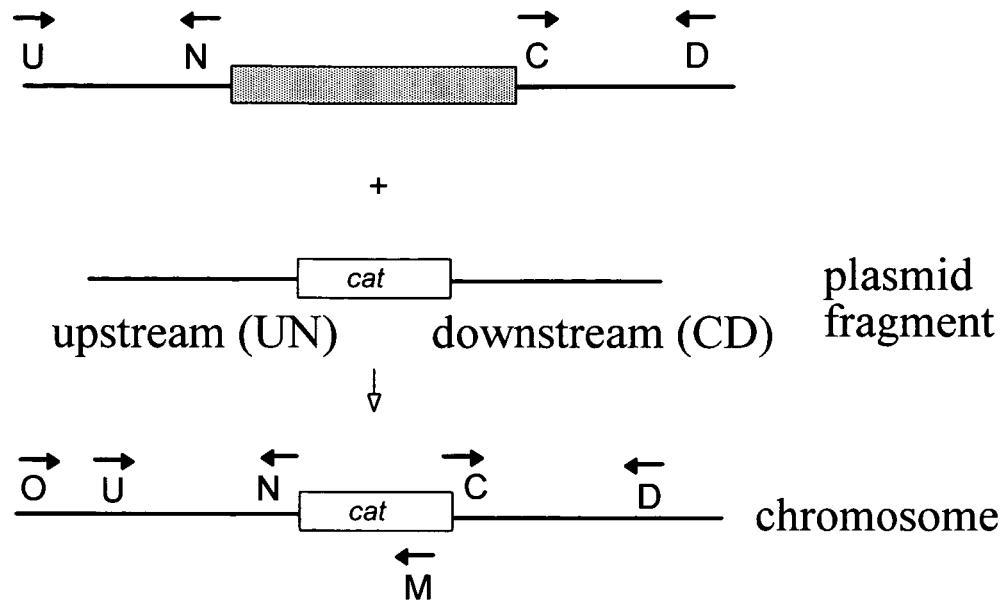
FIG. 1. Schematic showing substrates used for λ Red-mediated recombination, and the relative positions of various PCR primers used to generate the substrates and/or verify the structures of chromosomal gene replacements. Chromosomal gene replacements were verified by PCR using primers complementary to sequences upstream (U), downstream (D), N-terminal (N) or C-terminal (C) to the replaced gene, outside the region targeted by PCR (O), within the drug marker (M) and/or within the target gene (T). The absence of the wild type locus (shaded grey) was verified for strains listed in Table 1.
Figure 1:
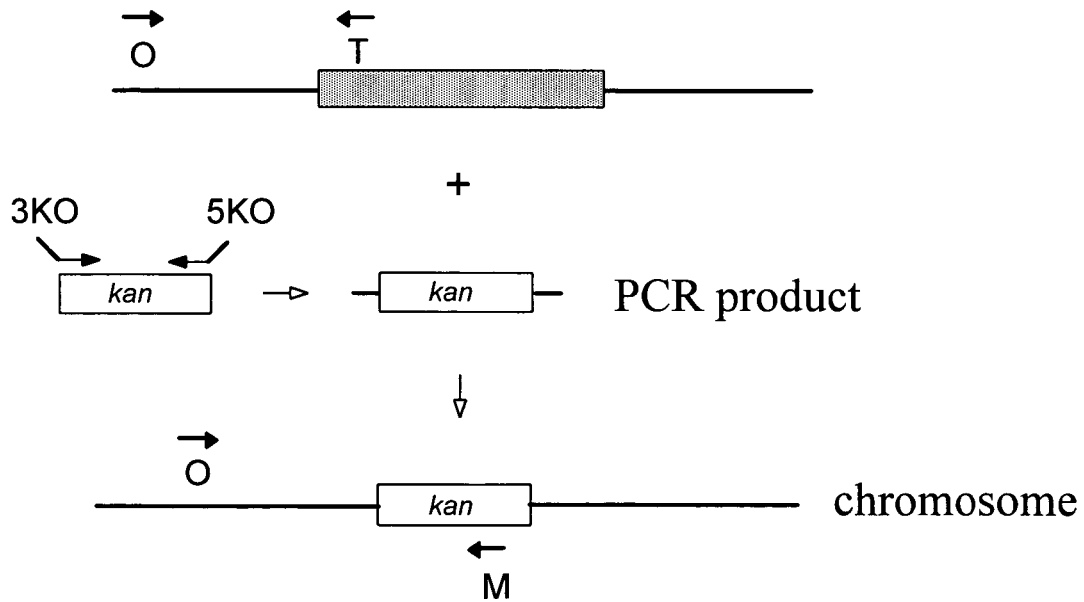

(A.) Plasmids containing marked deletions of target genes were generated as described in Table 2, using primers U, N, C and D as described previously (Murphy, et al., 2000). Plasmid digests (or purified DNA fragments) containing a drug marker flanked by 1-1.5 kb of sequences upstream and downstream of the target gene were electroporated into EHEC and EPEC cells containing Red-producing plasmid pTP223.

(B.) PCR products, containing a drug marker flanked by 40-60 bp of target DNA, were generated by primers designated 3KO and 5KO (see Table 3) and electroporated into EHEC containing pKM201 or pKM208 (or EPEC containing pTP223).

FIG. 2. Plasmid-borne tir is expressed and translocated at higher levels than chromosomally-encoded tir.

(A.) Tir molecules expressed in EPEC are depicted. EHEC Tir sequences are shown in open boxes, EPEC Tir sequences are shown in shaded boxes, and N-terminal HA-epitope tags are shown in black. Tir-PPP is wild type EPEC Tir; chimeric Tir-PHP consists of the N- and C-terminal cytoplasmic domains of EPEC Tir and the extracellular (intimin-binding) domain of EHEC Tir; chimeric Tir-HHH$_{NBS}$ contains the twelve amino acid Nck-binding site of EPEC Tir in the context of an otherwise EHEC Tir. Each of these versions of Tir were encoded on a low copy number plasmid in strain KC26, an EPEC strain which expresses the EHEC versions of cesT and eae and contains an in-frame deletion of tir (Campellone et al., 2002). Alternatively, each of these versions of tir were inserted into the chromosome of KC13 at the endogenous Tir locus (see Experimental Procedures).

(B.) HeLa cells were infected with EPEC strains expressing three HA-tagged versions of Tir depicted in (A) either chromosomally or on plasmids. Non-intimately associated bacteria were killed with gentamicin, and the remaining infected HeLa cell monolayers were collected, processed by immunoblot, and probed with anti-HA antiserum to visualize Tir. Blots were also probed with anti-N-WASP and anti-OmpA antisera to identify the relative cellular and bacterial protein levels, respectively, in each sample. HeLa cell lysates infected with strains harboring tir on a plasmid ("P") contain higher protein levels of bacterially-associated (~78 kDa) Tir, as well as greater levels of translocated (~90 kDa) Tir, than lysates infected with strains harboring tir encoded chromosomally ("C").

FIG. 3. EPEC expressing chromosomally-encoded Tir-HHH$_{NBS}$ generates pedestals of increased length on mammalian cells.

(A.) HeLa cells were infected with EPEC expressing plasmid-derived Tir molecules and examined microscopically. Monolayers were stained with anti-HA antiserum to visualize translocated Tir (green) and TRITC-phalloidin to visualize F-actin (red). F-actin staining indicated that each version of Tir triggered the formation of pedestals of similar appearance.

(B.) HeLa cells were infected with EPEC expressing chromosome-derived Tir molecules and examined microscopically. Monolayers were processed as in (A). F-actin staining indicated that bacteria expressing chromosomally-derived Tir-HHH$_{NBS}$ generated pedestals of greater lengths than other Tir molecules.

Figure 4:
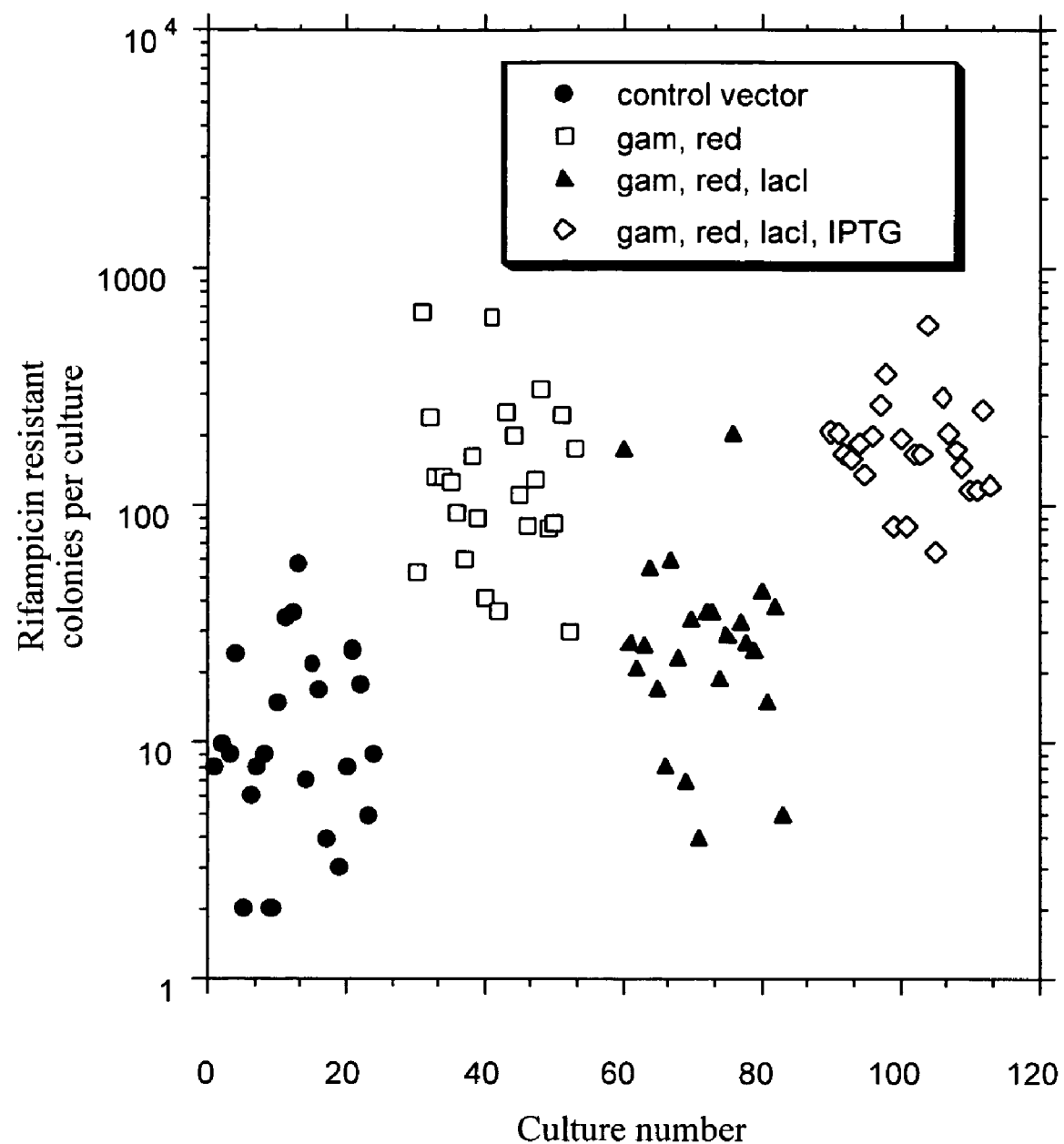

FIG. 4. Uncontrolled λ Red expression is mutagenic. A single fresh colony of EHEC (with indicated plasmids) was suspended in 1 ml LB containing 100 µg ml$^{-1}$ ampicillin. The cell suspension was diluted with LB-ampicillin to a final concentration of 5×10$^4$ cells/ml and aliquoted to 24 culture tubes. Overnight cultures (0.3 ml each) of EHEC strain TUV93-0 with control plasmid (circles), pKM201 (squares), pKM208 (triangles) and pKM208 with IPTG added (diamonds) were plated on LB plates containing 100 µg ml$^{-1}$ rifampicin. Plates were incubated overnight at 37 degrees and rifampicin resistant colonies were counted 24 hours later.

Figure 5:
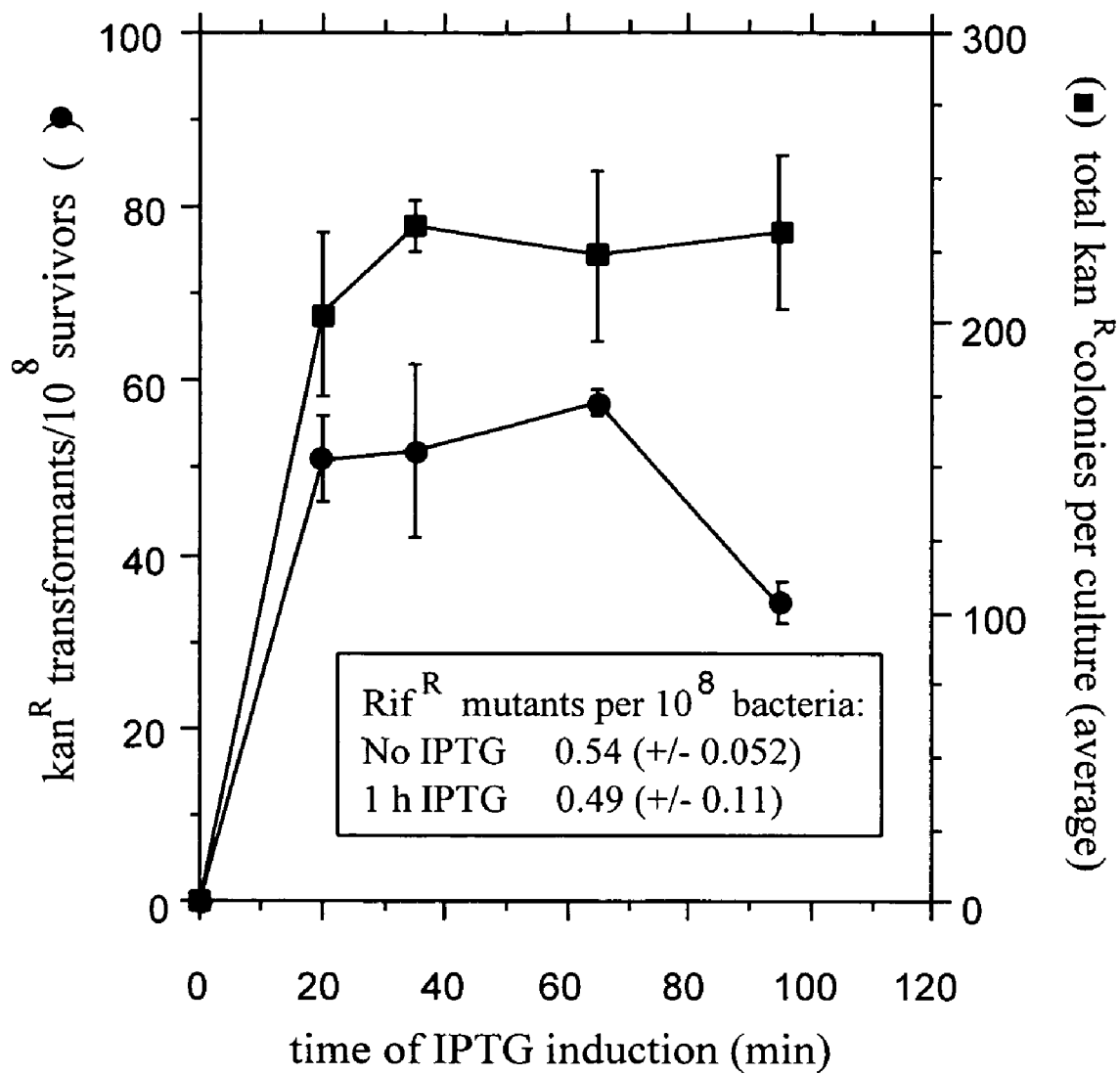

FIG. 5. Time course for promotion of hyper-rec phenotype. EHEC strain TUV93-0 containing pKM208 (five cultures, 20 ml each) was grown for electrocompetence as described in Experimental Procedures. At various times prior to collection, IPTG was added to four of the cultures to a final concentration of 1 mM; the fifth culture received no IPTG. The cells were heat shocked for the final 15 minutes, prepared for electroporation and electroporated with DNA (~0.25 µg) containing the kan gene flanked by 40 bp of EHEC DNA (resulting in a deletion of O-islands #130 and #131). After suspension in LB, the cells were grown for 90 minutes at 37° C., and plated on LB plates containing 20 µg ml$^{-1}$ kanamycin. The number of kan$^R$ transformants per 10$^8$ survivor and total number of kan$^R$ transformants are plotted as a function of IPTG concentration. The data points are averages of two experiments (ranges are shown). A random check of 160 colonies showed that 95% re-struck successfully to fresh LB plates containing 20 µg ml$^{-1}$ kanamycin; 10 of 10 of these colonies were verified by PCR analysis to be true recombinants (data not shown). Insert: 0.1 ml of electrocompetent cells, prepared with and without 1 hour IPTG induction, were spread on LB plates containing 100 µg/ml rifampicin to determine total number of Rif$^R$ mutants. Dilutions of the cells were titered on LB plates to determine total cell number; experiments done in triplicate (+/− standard error).

DETAILED DESCRIPTION OF THE INVENTION

The λ Red recombineering technology has been used extensively in *Escherichia coli* and *Salmonella typhimurium* for easy PCR-mediated generation of deletion mutants, but less so in pathogenic species of *E. coli* such as EHEC and EPEC.

The present invention is based, at least in part, on the identification of factors that improve the efficiency of Red recombineering in these pathogenic strains of *E. coli*. The inventors have identified conditions that optimize the use of λ Red for recombineering in EHEC and EPEC. Using plasmids that contain a P$_{tac}$-red-gam operon and a temperature-sensitive origin of replication, multiple mutations (both marked and unmarked) were generated in known virulence genes. In addition, five O157-specific islands (O-islands) of EHEC suspected of containing virulence factors were easily deleted. The inventors have discovered that the both PCR-generated substrates (40 bp of flanking homology) and plasmid-derived substrates (~1 kb of flanking homology) work well, each providing particular advantages. The establishment of the hyper-rec phenotype requires only a 20 minute IPTG induction period of red and gam. This recombinogenic window is important as constitutive expression of red and gam induces a 10-fold increase in spontaneous resistance to rifampicin. Other factors such as the orientation of the drug marker in recombination substrates and heat shock effects also play roles in the success of Red-mediated recombination in EHEC and EPEC.

Thus, in the present invention, the λ Red recombineering technology has been optimized for use in pathogenic species of *E. coli*, namely EHEC and EPEC. Exemplifying the utility of this technology, five O-islands of EHEC were easily and precisely deleted from the chromosome by electroporation with PCR-generated substrates containing drug markers flanked with 40 bp of target DNA. The discoveries described herein are applicable to λ Red recombineering in these and other strains of pathogenic bacteria for faster identification of virulence factors and the speedy generation of bacterial mutants for vaccine development.

Accordingly, the present invention features improved methods and systems for promoting recombination in bacteria. In particular, the invention features an improved λ Red recombination system. This improved system is particularly suited for recombination in pathogenic strains of bacteria. In particular, the invention features isolated nucleic acid molecules and vectors encoding bacteriophage recombinases, e.g., bacteriophage λ Red and Gam, which are operably linked to a promoter, e.g., Ptac promoter, and the LacI repressor. The bacteriophage recombinases promote homologous recombination between nucleic acid material. Preferably the vectors of the invention further consist of a temperature-sensitive origin of replication that confers low copy number upon the vector.

A featured vector of the invention is pKM208. pKM208 expresses Red and Gam and possesses a low copy number replicon which is temperature sensitive. Red and Gam are expressed from the Ptac promoter, a promoter capable of directing high levels of expression of the red and gam genes. High levels of Red and Gam result in efficient gene replacement, preferably, when this plasmid is used in pathogenic bacteria (e.g., pathogenic *E. coli* species). The data exemplified herein shows that pKM208 promotes both long and short homology gene replacement in enterohemorrhagic *E. coli* 0157:H7 (EHEC, a pathogen for come concern in the cattle industry).

The present invention also features recombinant organisms, e.g., bacteria or pathogenic bacteria, which contain vectors of the present invention and methods of using the recombinant organisms to promote efficient recombination of genetic material.

The recombination systems of the invention are particularly useful in drug target validation. For example, the systems can be used to make knockouts of suspected virulence and/or essential genes, thereby identifying potential drug targets. The recombination systems are also useful in vaccine development, in particular, in the development of vaccines against *E. coli* pathogens. The systems are also useful for in vivo cloning. In particular, the systems can be used for the cloning of vaccine antigens against EHEC.

In order that the present invention may be more readily understood, certain terms are first defined herein.

The term "nucleic acid molecule" refers to a polymer of nucleotides, preferably, deoxyribonucleotides or ribonucleotides or analogs of said nucleotides, for example, analogs having modified binding properties and/or metabolic properties. The term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated EPK-55053 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The term "gene", as used herein, includes a nucleic acid molecule (e.g., a DNA molecule or segment thereof), for example, a protein- or RNA-encoding nucleic acid molecule, that in an organism, is separated from another gene or other genes, by intergenic DNA (i.e., intervening or spacer DNA which naturally flanks the gene and/or separates genes in the chromosomal DNA of the organism). A gene may direct synthesis of an enzyme or other protein molecule (e.g., may comprise coding sequences, for example, a contiguous open reading frame (ORF) which encodes a protein) or may itself be functional in the organism, e.g., may function as a recognition sequence for proteins in the organism. A gene in an organism, may be clustered in an operon, as defined herein, said operon being separated from other genes and/or operons by the intergenic DNA. Individual genes contained within an operon may overlap without intergenic DNA between said individual genes.

An "isolated gene", as used herein, includes a gene which is essentially free of sequences which naturally flank the gene in the chromosomal DNA of the organism from which the gene is derived (i.e., is free of adjacent coding sequences which encode a second or distinct protein or RNA molecule, adjacent structural sequences or the like) and optionally includes 5' and 3' regulatory sequences, for example promoter sequences and/or terminator sequences. Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

Genes can be obtained from a variety of sources, including cloning from a source of interest or synthesizing from known or predicted sequence information, and may include sequences designed to have desired parameters.

A DNA segment is "operably linked" when placed into a functional relationship with another DNA segment. For example, DNA encoding a signal peptide is operably linked to DNA encoding a protein or polypeptide if, when expressed, the sequences encode the signal peptide in frame with the protein or polypeptide. Likewise, a promoter or enhancer is operably linked to DNA encoding a protein or polypeptide if expression of the protein or polypeptide is promoted or enhanced. In one embodiment, DNA sequences that are operably linked are contiguous (e.g., in the case of a signal sequences). Alternatively, DNA sequences that are operably linked can be non-contiguous (e.g., in the case of enhancers).

"Promoter" refers to a region of DNA involved in binding a polymerase (e.g., a RNA polymerase) to initiate transcription. An "inducible promoter" refers to a promoter that directs expression of a gene where the level of expression is alterable by environmental or developmental factors such as, for example, temperature, pH, transcription factors, activators, repressors and chemicals.

An "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be included. For example, transcription termination signals, enhancers, and other nucleic acid sequences that influence gene expression, can also be included in an expression cassette.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Alternatively, a vector can be linear.

The term "recombinant vector" includes a vector that has been altered, modified or engineered such that it contains greater, fewer or different nucleic acid sequences than those included in a naturally-occurring vector.

As used herein, "origin of replication sequences" refer to sequences which, when present in a vector, initiate replication. Origin of replication sequences "which confer low copy number on a vector" refer to sequences which, when present in a vector, direct replication of the vector such that it is maintained in the host cell/organism at a low copy number.

As used herein, a "temperature sensitive" origin of replication refers to a replication origin which is controlled by temperature, e.g., is rendered nonfunctional at a nonpermissive temperature and/or is functional at a permissive temperature.

As used here, the term "exogenous" refers to genetic material (e.g, nucleic acid material") that originates from a source foreign to the particular host organism, or, if from the same source, is modified from its original form. The term "endogenous" refers to genetic material (e.g, nucleic acid material) that originates from the host organism, i.e., that is naturally-occurring.

As used herein, "recombination" refers to a process by which nucleic acid material e.g., DNA, is exchanged between two nucleic acid molecules, for example, in a microorganism. As used herein, "homologous recombination" refers to a process by which nucleic acid material e.g., DNA, is exchanged between two nucleic acid molecules through regions or segments of sequence homology, or preferably, sequence identity (e.g., a high degree of sequence identity). In exemplary embodiments, the nucleic acid material, e.g., DNA, is located on a chromosome or an episome of the microorganism. In another exemplary embodiments, the nucleic acid material, e.g., DNA, is located extrachromasomally, for example, on a plasmid. Recombination can occur between linear and/or circular DNA molecules.

As used herein, "recombinase" refers to an enzyme, enzymatic activity or enzymatic function that catalyzes recombination. Preferred recombinases of the present invention catalyze homologous recombination. Particularly preferred recombinases of the present invention are bacteriophage recombinases, for example, the bacteriophage λ Red recombinase (encoded by exo and bet nucleotide sequences).

As used herein, "anti-recombinase" refers to inhibitor of a recombinase activity endogenous to the host organism. Preferred anti-recombinases of the invention are bacteriophage anti-recombinases (e.g., the bacteriophage anti-recombinase encoded by gam) which inhibits RecBCD in the host organism.

As used herein, the phrase "recombination segments" refers to segments of nucleic acid material (e.g., DNA) that are sufficiently homologous or identical to target nucleic sequences, for example, sequences present in or within the vicinity of a gene present in a microorganism (e.g., within <1 kB of the gene), such that the segment directs recombination at the target nucleic acid sequence. The recombination segments are routinely separated by nucleic acid material (e.g., DNA) that is to be integrated at the target site. Recombination segments routinely are recognized by the recombinase enzymes described herein. Recombination segments are preferably between 40-60 base pairs (bp) in length, i.e., are homologous or identical to a region of target DNA of between 20-80, 30-70, or 40-60 bp in length (e.g., 50 bp in length).

As used herein, an "integrating segment" refers to a nucleotide sequence that is to be integrated at a target recombination site in nucleic acid of a microorganism. The integrating segment can be random, e.g., spacer nucleic acid or, preferably, nucleic acid encoding for a selectable marker, e.g., ampicillin or kanamycin. An integrating segment useful in the present invention is flanked by recombination segments. As used herein, nucleic acid "flanked" by recombination segments indicates that the recombination segments are located 5' and 3' to the nucleic acid (e.g., left and right arms).

As used herein, the term "substrate" refers to nucleic acid material, e.g., DNA, that includes at least recombination segments, as defined herein. Preferred substrates further include an integrating segment flanked by said recombination segments. A particularly preferred substrate is a linear double-stranded ("ds") or duplex DNA molecule. An exemplary substrate is less than 2.5 kb in length.

As used herein, the phrase "recombination proficient" refers to a microorganism in which homology-dependent or homologous recombination can occur. Notably, homologous recombination occurs at some level (e.g., at a baseline level) in naturally occurring microorganisms. Preferred "recombination proficient" microorganisms of the instant invention have been engineered such that homologous recombination occurs at a level greater than that observed in corresponding naturally occurring microorganisms. Recombinant microorganism which have been so engineered are also referred to herein as "hyper-recombination proficient" microorganisms.

As used herein, the term "derived from", when referring to a prokaryote or a eukaryote, includes a nucleic acid or gene which is naturally found in a prokaryotic organism or a eukaryotic organism. Preferably, the nucleic acid or gene is derived from a microorganism, e.g., a bacteria, e.g., *Escherichia coli*. The term "bacterially-derived" or "derived-from", for example bacteria, includes a gene which is naturally found in bacteria or a gene product (e.g., an enzyme) which is encoded by a bacterial gene.

The term "operon" includes a coordinated unit of gene expression that contains a promoter and possibly a regulatory element associated with one or more, preferably at least two, structural genes (e.g., genes encoding enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, a single promoter and/or regulatory element can control expression of each gene product encoded by the operon.

I. Bacteriophage Recombinase Functions and Recombination-Promoting Vectors

The present invention features recombination-promoting vectors for use in a variety of recombination methods. The vectors include sequences encoding bacteriophage recombinases, e.g., bacteriophage λ Red and Gam, which are operably linked to a promoter, e.g., Ptac promoter, and the LacI repressor. The bacteriophage recombinases promote homologous recombination between nucleic acid material. Preferably the vectors of the invention further consist of a temperature-sensitive origin of replication that confers low copy number upon the vector.

The nucleic acid molecules and vectors of the present invention provide a bacteriophage recombinase and/or anti-recombinase function. In preferred embodiments, the bacteriophage recombinase function is a bacteriophage λ Red recombinase function and the antirecombinase function is a λ Red antirecombinase function.

The nucleic acid molecules and vectors of the invention preferably include nucleotide sequences encoding the bacteriophage λ gene product Exo or a functional equivalent thereof, Bet or a functional equivalent thereof, and Gam or a functional equivalent thereof. The exo, bet and gam genes (and their corresponding gene products) are well known to those skilled in the art and the coding sequences of those genes have the following GenBank accession numbers: (1) exo gene: ACCESSION NC_001416, REGION complement (31348 . . . 32028), VERSION NC_001416.1 GI:9626243, Gene ID: 2703522, (SEQ ID NO: 35); (2) bet gene: ACCESSION NC_001416, REGION complement (32025 . . . 32810), VERSION NC_001416.1 GI:9626243, Gene ID: 2703535, (SEQ ID NO: 36); (3) gam gene: ACCESSION NC_001416, REGION complement (32816 . . . 33232), VERSION NC_001416.1 GI:9626243, Gene ID: 2703509, (SEQ ID NO: 37). The corresponding amino acid sequences have the following GenBank accession numbers: Exo: Accession no: NP_040616—GI:9626280; Bet—Accession no: NP_040617—GI:9626281; Gam—Accession no: NP_040618—GI:9626282.

As used herein the term "functional equivalent" refers to gene product which can provide a similar enzymatic activity to the gene products having the GenBank accession numbers given above. A functional equivalent of Exo, Bet or Gam has a similar enzymatic activity in the sense that it catalyses the same reaction with substantially the same specificity as Exo, Bet or Gam and catalyses that reaction at a rate of at least 60%, at least 70%, preferably at least 80%, generally at least 90%, for example at least 95%, typically at least 99% and most preferably at a rate substantially the same as that of Exo, Bet or Gam when measured under the same conditions.

Functional equivalents of Exo, Bet or Gam may be obtained by any method known to those skilled in the art. For example, they can be generated by nucleotide substitutions of the wild type sequence of exo, bet or gam, for example from 1, 2 or 3 to 10, 25, 50 or 100 substitutions. Wild type sequences may alternatively or additionally be modified by one or more insertions and/or deletions and/or by an extension at either or both ends to give functional equivalents. The modified polynucleotide typically encodes a gene product which has activity as defined above.

Degenerate substitutions may be made and/or substitutions may be made which would result in a conservative amino acid substitution when the modified sequence is translated. Typically a functional equivalent will share at least 70% identity, at least 80% identity, at least 90% identity, at least 95% identity, or at least 99% identity with the wild type Exo, Bet or Gam sequence over at least 20, preferably at least 30, for instance at least 40, at least 60, or more preferably at least 100 contiguous amino acids or most preferably over the full length of the wild type Exo, Bet or Gam sequence.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at on line through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers, E. and Miller, W. (*Comput. Appl. Biosci.* 4:11-17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to exo, bet or gam nucleic acid molecules of the invention. BLAST protein searches can be performed with the XBLAST program, score=100, wordlength=3, and a Blosum62 matrix to obtain amino acid sequences homologous to Exo, Bet or Gam polypeptide molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See the website for the National Center for Biotechnology Information.

A functional equivalent may also be capable of hybridizing under stringent hybridization conditions to a complement of the wild type exo, bet or gam sequence. Such stringent conditions are known to those skilled in the art and can be found in *Current Protocols in Molecular Biology*, Ausubel et al., eds., John Wiley & Sons,. Inc. (1995), sections 2, 4, and 6. Additional stringent conditions can be found in *Molecular Cloning: A Laboratory Manual*, Sambrook et al, Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2×SSC, 1% SDS.

A sequence which can hybridize to the complement of its corresponding sequence can typically hybridize to that coding sequence at a level significantly above background. The signal level generated by the interaction between a functional equivalent and the complement of its corresponding sequence is typically at least 10 fold, preferably at least 100 fold, as intense as interactions between other sequences and the Exo, Bet or Gam coding sequences.

In preferred embodiments the promoters are regulated, because the exo, bet and gam genes or functional derivatives of any thereof can then be expressed only when homologous recombination is required. This may help to reduce any unwanted recombination events mediated by the exo, bet and gam polypeptides or polypeptides similar thereto. In preferred embodiments, a promoter such as Ptac in combination with LacI repressor may be used.

It is also within the scope of the invention that a prophage can be used to express exo, bet and gam (or genes encoding functional derivatives of any thereof). If a prophage is used to express exo, bet and gam (or functional derivatives), it may be convenient to engineer controlled expression using the cI-repressor. Use of this system allows expression of exo, bet, and gam to be controlled by temperature. Growth of cells containing the prophage at 32° C. results in no expression of exo, bet and gam, whereas growth of cells containing the prophage at 42° C. results in expression of exo, bet and gam. Use of such a system may require cells containing the prophage to be grown to be at the permissive temperature for a short time, for example from 2 to 30 minutes, for example from 5 to 15 minutes, before transfer of the construct into the cells.

Vectors which include sequences encoding other bacteriophage recombinases (e.g, Rac prophage recombinases encoded by the RecE and RecT genes) are also contemplated within the scope of the instant invention.

II. Substrates

In a preferred embodiment, the substrates for use in the recombination methods of the invention comprise an integrating segment flanked by recombination segments, wherein the recombination segments are homologous to the target bacterial gene or surrounding sequences A. Recombination Segments Recombination segments typically flank an integrating segment when in a substrate of the invention and will flank a target nucleotide sequence upon recombination. Such sequences have to be sufficiently similar to the corresponding sequence in the bacterium and of sufficient length for homologous recombination to occur between the substrate and the bacterial chromosome. Typically, recombination segments will be sufficiently dissimilar from each other such that recombination of the target sequence occurs in a selected orientation.

Recombination segments do not need to be of the same length. In general, recombination segments may be, independently, at least 10 bp in length, at least 20 bp, at least 50 bp in length, at least 60 bp in length, at least 75 bp in length or at least 100 bp in length. Typically, recombination segments will be, independently, up to 200 bp in length, up to 300 bp in length, up to 500 bp in length, up to 750 bp in length, up to 1 kb in length or up to 2 kb in length.

Typically, recombination segments for use in the invention will share 100% identity over their entire length with the target sequence to which they correspond (e.g., the corresponding on the bacterial chromosome). However, recombination segments suitable for use in the invention may share, independently, at least 60% identity, at least 70% identity, at least 80% identity, at least 90% identity, at least 95% identity, or at least 99% identity with the corresponding bacterial sequence over a contiguous stretch of nucleotides representing at least 50% of its length, at least 60% of its length, at least 70% of its length, at least 80% of its length, at least 90% of its length, at least 95% of its length or at least 99% its length. Any combination of the above mentioned percentage identity and percentage length may be used to define a recombination segment suitable for use in the invention, with greater % identity to the corresponding sequence on the bacterial chromosome over a greater percentage of the length of the sequence being preferred.

A suitable recombination segments may also be capable of hybridizing under stringent conditions to the complement of the sequence to which it corresponds on the bacterial chromosome. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4×sodium chloride/sodium citrate (SSC), at about 65-70° C. (or alternatively hybridization in 4×SSC plus 50% formamide at about 42-50° C.) followed by one or more washes in 1×SSC, at about 65-70° C. Other preferred, non-limiting examples of stringent hybridization conditions are as described herein.

The λ Red-promoted recombination methods of the invention can be carried out using substrates comprising short recombining segments, e.g., individually, about 40-60 bp. A substrate of the invention comprising short recombination segments can be a PCR-generated substrate. PCR methodologies to produce such substrates are commonly known in the art, and would be apparent to the skilled artisan. PCR-generated substrates offer a simple mechanism for generating gene knockouts. The λ Red-promoted recombination methods of the invention can be carried out using substrates comprising long recombining segments, e.g., individually, up to about 1 kb or 2 kb or more. A substrate of the invention comprising long recombination segments can be a vector or plasmid. Long homology-containing vector, e.g., plasmid, substrates provide advantages, for example, when multiple mutant alleles of a target gene need to be crossed into the chromosome. When multiple mutant alleles of the target gene will be crossed into the chromosome, it is desirable to have the substrate previously cloned, in order to not induce PCR errors into the allele prior to transfer to the chromosome. A dedicated plasmid containing sequenced regions upstream and downstream regions of the target gene is required. Typically, long homology-containing substrates promote higher frequencies of gene replacement relative to short homology substrates. Typically, long homology-containing substrates offer higher success rates for Red-promoted gene replacement in pathogenic hosts that are not as electrocompetent as *E. coli* K-12.

B. Integrating Segment

The integrating segment may be any sequence with which it is desired to replace the target sequence. The integrating segment does not need to be the same length as the target sequence and can be shorter or longer than the target sequence. In one embodiment, the integrating segment and target sequence are similar in length, for example, the integrating segment may be 50%, 60%, 70%, 80%, 90%, 95% or substantially the same length of the target sequence or vice versa. It will be convenient for the integrating segment to comprise a coding sequence which codes for a polypeptide which is readily detectable (i.e., a marker polypeptide), so that bacteria in which homologous recombination has occurred can be easily identified. If the integrating segment comprises a coding sequence, it will also typically comprise a promoter operably linked to that coding sequence. The promoter should be selected so that expression of the coding sequence will be driven in the bacterium into which the construct is transferred.

Exemplary marker polypeptides include drug markers, for example, polypeptides that confer resistance to kanamycin, ampicillin or tetracycline. Alternatively, the marker is a reporter polypeptide. Such a polypeptide may be, for example, a fluorescent or a colorimetric polypeptide. Such polypeptides are easy to detect using techniques will known to those skilled in the art.

If the marker confers antibiotic resistance on the bacterium, then candidate bacteria can be grown in the presence of the antibiotic. Only bacteria which have successfully incorporated the integrating segment will be able to grow in the presence of the antibiotic. Alternatively, if the marker is a gene encoding a fluorescent polypeptide, for example green fluorescent protein, fluorescence may be used to indicate the presence of the integrating segment.

Substrates for use in the invention can be prepared using, for example, recombinant DNA technology well known to those skilled in the art. Typically, it will be convenient to prepare Substrates using polymerase chain reaction (PCR). Primers may be designed which comprise sequences corresponding to the recombination segments.

The primers described above may be used in PCR on a template which comprises the integrating segment to generate a linear substrate suitable for use in the invention. PCR can be carried out on, for example, a plasmid which contains the integrating segment and the linear PCR product obtained can then be purified from the PCR—reaction mixture. It may, however, be more convenient to isolate the integrating segment as a linear fragment and to carry out PCR on that fragment. Use of this latter technique is advantageous over a technique which carries out PCR directly on a plasmid, because no purification of the construct is required after PCR. In order to ensure that the plasmid does not interfere with the subsequent transfer and selection (if selection is used), the resulting PCR reaction has to undergo a rigorous purification scheme involving: (1) gel purification; (2) digestion with a restriction endonuclease; and (3) a further round of gel purification. Such steps are not required if PCR is carried out on a linear template.

The use of single stranded DNA (ssDNA) substrates and/or vectors is also within the scope of the invention.

III. Recombination

The substrate can be introduced into a recombination-proficient bacteria by any suitable method. Suitable methods are will known to those skilled in the art, for example electroporation or thermal shock. Homologous recombination between the substrate and a target sequence in the bacteria leads to replacement of the target sequence with the integrating segment of the substrate.

A target sequence may comprise all or part of a bacterial gene, for example, the target sequence may comprise all or part of a control sequence, such as a promoter, or may comprise or all or part of a coding sequence. The target sequence may be of any suitable size, for example from about 1 bp to about 50 kb in length. Typically, however, the minimum size of a target sequence will be at least 10 bp, at least 25 bp, at least 50 bp or more, preferably at least 100 bp or typically at least 500 bp in length. In general the maximum length of a target sequence will be up to 30 kb, up to 15 kb, up to 5 kb or up to 2 kb. The length of the target sequence may preferably be up to 1 kb and typically up to 800 bp. Any combination of the above mentioned lower and upper lengths may be used to defined a target sequence of the invention. Recombination segments are preferably within the vicinity of a target gene (e.g., within at least about <1 kb, 2 kb, 5 kb, 10 kb, 20 kb or more of the target gene). Notably, however, the λ Red systems of the invention are capable of recombining nucleic acid segments as large as 10 kb, 20 kb, 30 kb, 40 kb, 50 kb or more.

IV. Host Organisms

The invention may be carried out using any bacteria. For example, the bacteria may be a Gram-positive bacteria (i.e., a bacteria which retains basic dye, for example, crystal violet, due to the presence of a Gram-positive wall surrounding the microorganism) or a Gram-negative bacteria (i.e., excludes basic dye). Preferred bacteria are pathogenic bacteria. The bacteria may be pathogenic for a human or an animal or for a plant.

The bacteria may be for example, from the genus *Escherichia*. Preferred pathogenic bacteria are from the *E. coli* species. Enterohemorrhagic *E. coli* O157:H7 (EHEC) and enteropathogenic *E. coli* (EPEC) are members of the attaching and effacing (AE) family of enteric pathogens (reviewed by Nataro and Kaper, 1998 and Vallance et al., 2002). These pathogens bind tightly to the intestinal epithelium and cause localized effacement of micovilli, followed by alteration of the cytoskeleton beneath sites of bacterial attachment. The result of this process is the formation of a filamentous structure known as an actin pedestal (Frankel et al., 1998). The presence of these cause of a spectrum of diseases in humans ranging from gastroenteritis to fatal septicemic disease; *Bordetella pertussis*—the cause of whooping cough; *Brucelia abortus*—a cause of abortion and infertility in cattle and a condition known as undulant fever in humans; *Vibrio cholerae*—a cause of cholera; *Clostridium tetani*—a cause of tetanus; and *Bacillus anthracis*—a cause of anthrax.

V. Uses

The invention provides a general method for promoting efficient recombination of genetic material in a microorganism, e.g., a bacteria, preferably a pathogenic bacteria. The methods provided in the invention can be used to replace a specific genomic sequence in a bacterium with any other desired sequence present in a substrate, as defined herein. The methods of the invention can also be used to replace a specific sequence present on an episome in a bacterium with any other desired sequence present on a substrate. When the specific sequence to be replaced is present on an episome in a bacterium, that sequence can be derived, e.g., from a prokaryote or a eukaryote.

Several rounds of recombination of genetic material according to the invention may be carried out sequentially, each time using a different substrate. Alternatively, more than one, for example, two, three, four, five or more, substrates for use in the invention can be transferred simultaneously into a bacterium. Thus, a bacterium produced using methods of the invention may comprise mutations in more than one, for example two, three, four, five or more, genes.

After successful recombination, it may be necessary to eliminate the integrating segment from the genetically modified bacterium. This may be required if the genetically modified bacterium is to be used in or as a vaccine. For example, the use of antibiotic resistance genes in live attenuated bacteria is not generally permitted by regulatory authorities.

A construct of the invention may therefore also comprise sequences which may be used to eliminate the integrating segment. Such sequences will typically flank the integrating segment and will generally be positioned between the first recombination segment and the integrating segment and between the second recombination segment and the integrating segment.

The present invention further provides methods for determining whether a bacterial gene is a potential drug target. For example, the method allows null mutants to be created, and thus provides an important tool in the analysis of genes for which no function is known. If a particular sequence, for example an open reading frame or a part thereof or a region 5' to an open reading frame (for example a promoter) or part thereof, cannot be replaced, that may indicate that the sequence is essential for viability in the bacterium in which the sequence occurs, i.e. that the sequence represents all or part of an essential gene. An essential gene is a gene which, when missing (e.g., because of a chromosomal deletion) or mutated to render it non-functional, results in a lethal phenotype. That is, a gene without which a bacteria cannot survive. Essential sequences are targets for the development of new antibiotics. For example, bacterial genes identified as new drug targets by the methods of the present invention are used in screening assays for new antimicrobial substances.

The use of bioinformatics may allow the rapid isolation of further essential genes, i.e. corresponding genes from other bacterial species. A gene identified from a particular species by using the methods of the invention may be used to search databases containing sequence information from other species, in order to identify orthologous genes from those species. Genes so identified can then be tested for whether they are essential by using the genetic recombination methods of the invention. For example, if an *E. coli* gene is identified as essential using a method as described above, this may allow the identification of a putative orthologue from *Salmonella*. That *Salmonella* gene may be tested by using the genetic recombination methods of the present invention. Further orthologues may be identified in more distantly related organisms.

Suitable bioinformatics programs are well known to those skilled in the art. For example, the Basic Local Alignment Search Tool (BLAST) program (Altschul et al., 1990, J. Mol. Biol. 215, 403-410 and Altschul et al., 1997, Nucl. Acids Res. 25, 30 3389-3402.) may be used. Suitable databases for searching are for example, EMBL, GENBANK, TIGR, EBI, SWISS-PROT and trEMBL.

The methods and systems of the invention are also useful in gene repair and replacement methodologies. The methodologies of the invention are also useful in in functional genomics strategies designed to analyze the genomes of microorganisms, i.e., to determine the function of unknown genes. Alternatively, sequences of known function may be recombined to produce modified bacteria having desired properties.

The systems and methodologies of the invention are also useful in analyzing bacterial pathogenic mechanisms. In an exemplary embodiment, a gene can be mutated that results in attenuation of a pathogenic bacterium. Such attenuated bacteria may be used in the preparation of vaccines for use, for example, in humans or animals.

The systems and methodologies of the invention are also useful in in vivo cloning applications (e.g., in gap filling applications) and/or marker rescue applications.

VI. Antigens and Vaccines

The recombination methods of the present invention may be used to prepare attenuated live vaccines. The principle behind vaccination is to induce an immune response in the host thus providing protection against subsequent challenge with a pathogen. This may be achieved by inoculation with a live attenuated strain of the pathogen, i.e. a strain having reduced virulence such that it does not cause the disease caused by the virulent pathogen. Typically, attenuation is achieved by mutating genes which are required for virulence/pathogenicity or viability in a host.

The recombination methods of the invention may be used to introduce mutations into a bacterium which result in attenuation of that bacterium. The attenuated bacterium can then be used in a vaccine. The bacterium which is attenuated using recombination methods of the invention can contain a non-reverting mutation in at least one gene, for example, one, two, three, four, five or more, which is required for pathogenicity.

The mutations introduced into a bacterium for use in a vaccine generally knock-out the function of the gene completely. This may be achieved either by abolishing synthesis of any polypeptide from the gene or by making a mutation that results in synthesis of non-functional polypeptide. In order to abolish synthesis of a polypeptide, either the entire gene or part of the gene, e.g., its 5'-end, may be replaced using the recombination methods of the invention. Alternatively, the recombination methods of the invention may be used to introduce insertions or deletions into the coding sequence of a gene to create a gene that encodes a non-functional peptide (e.g., polypeptide that contains only the N-terminal sequence of the wild-type protein). The recombination methods of the invention may also be used to introduce mutations, e.g., point mutations, into the sequence of a gene to create a gene that encodes a non-functional peptide (e.g., a mutation introducing a stop codon into a gene such that a truncated protein is produced). The bacterium may have mutations in one or more, for example, one, two, three or four genes. The mutations are non-reverting mutations. These are mutations that show essentially no reversion back to the wild-type when the bacterium is used as a vaccine. Such mutations are typically insertions and deletions. Insertions and deletions are preferably large, typically at least 10 nucleotides in length, for example from 10 to 600 nucleotides. Preferably, the whole coding sequence is deleted.

Deletions may be carried out by replacing a target coding sequence with an integrating segment and then subsequently removing the integrating segment as is described above. The bacterium used in the vaccine preferably contains only defined mutations, i.e. mutations which are characterized. It is clearly undesirable to use a bacterium which has uncharacterized mutations in its genome as a vaccine because there would be a risk that the uncharacterized mutations may confer properties on the bacterium that cause undesirable side-effects.

In addition, if the bacterium is to be used in a vaccine and the exo, bet and gam genes are expressed from a plasmid, it is preferable to remove the plasmid before the bacterium is used in vaccination. There a number of ways of removing plasmids, which are well known to those skilled in the art. For example, the plasmid expressing exo, bet and gam may be temperature sensitive (ts). Thus, a ts-replicon may be included in the plasmid. The use of plasmids including a ts-replicon allows recombination to be carried out in cultures grown at permissive temperature (e.g., 30° C.). Following recombination of genetic material, the growth temperature of the *E. coli* host can be raised to a non-permissive temperature (e.g., 43° C.). Under these conditions, the replicon cannot function, and consequently colonies can be isolated that are plasmid-free.

The attenuated bacterium of the invention may be genetically engineered to express an antigen that is not expressed by the native bacterium (a "heterologous antigen"), so that the attenuated bacterium acts as a carrier of the heterologous antigen. The antigen may be from another organism, so that the vaccine provides protection against the other organism. A multivalent vaccine may be produced which not only provides immunity against the virulent parent of the attenuated bacterium but also provides immunity against the other organism. Furthermore, the attenuated bacterium may be engineered to express more than one heterologous antigen, in which case the heterologous antigens may be from the same or different organisms. The heterologous antigen may be a complete protein or a part of a protein containing an epitope. The antigen may be from a virus, prokaryote or a eukaryote, for example another bacterium, a yeast, a fungus or a eukaryotic parasite. The antigen may be from an extracellular or intracellular protein.

A DNA construct comprising the promoter operably linked to DNA encoding the heterologous antigen may be made and transformed into the attenuated bacterium using conventional techniques. Transformants containing the DNA construct may be selected, for example by screening for a selectable marker on the construct. Bacteria containing the construct may be grown in vitro before being formulated for administration to the host for vaccination purposes. The vaccine may be formulated using known techniques for formulating attenuated bacterial vaccines. The vaccine is advantageously presented for oral administration, for example in a lyophilized encapsulated fond. Such capsules may be provided with an enteric coating comprising, for example, Eudragate "S" (Trade Mark), Eudragate "L" (Trade Mark), cellulose acetate, cellulose phthalate or hydroxypropylmethyl cellulose. These capsules may be used as such, or alternatively, lyophilized material may be reconstituted prior to administration, e.g., as a suspension. Reconstitution is advantageously effected in a buffer at a suitable pH to ensure the viability of the bacteria. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramuscular administration.

The vaccine may be used in the vaccination of a mammalian host, particularly a human host but also an animal host. An infection caused by a microorganism, especially a pathogen, may therefore be prevented by administering an effective dose of a vaccine prepared according to the invention. The dosage employed will ultimately be at the discretion of the physician, but will be dependent on various factors including the size and weight of the host and the type of vaccine formulated. However, a dosage comprising the oral administration of from $10^7$ to $10^{10}$ bacteria per dose may be convenient for a 70 kg adult human host.

This invention is further illustrated by the following examples which should not be construed as limiting. The contents of all references, patents and published patent applications cited throughout this application are incorporated herein by reference.

EXAMPLES

General Methodology:

A. Strains and Plasmids

Strains used and generated in this study are listed in Table 1. The strain KC5 (EHECΔtir) has been previously cited (Campellone, et al., 2002); its construction is described here. KC12 is an EPEC strain expressing EHEC tir-cesT-eae; KC13 is a Δtir::cat-sacB version of KC12; KC26 is a Δtir version of KC12 (Campellone, et al., 2002). Strains expressing chromosomal versions of Tir were generated by electroporating KC13 with linear fragments derived from ApaLI-XhoI digestions of pKC17, pKC142, and pKC166 (see Tables 1 & 2). Plasmids pKM154, pTP550, pTP223, pTP806, pTP826, and Tir-expressing plasmids designated pTir-PPP (pKC17) and pTir-HHH$_{NBS}$ (pKC142) have been described previously (Murphy et al., 2000; Semerjian et al., 1989; Poteete and Fenton, 1984; Poteete et al., 1999; Campellone et al., 2002). pAMPts is an ampicillin derivative of pMAK705 (Hamilton et al., 1989). A Cam$^R$ version of pKM201 (pKM200) was also constructed and behaves similarly to pKM201. Plasmids constructed for this study are shown in Table 2.

A description of pKM208 and representative predecessors, is as follows:

pKM200 The Bgl II fragment from pTP806, containing Ptac-gam-red, was ligated to the Bam HI site in pMAK705. Temperature-sensitive red-gam expressing plasmid; Cam R.

pKM201 The Bgl II fragment from pTP806, containing Ptac-gam-red, was ligated to the BamHIsite in pAMPts. Temperature-sensitive red-gam expressing plasmid; Amp R.

pKM208 The Eco R-Pst I lacI-containing fragment from pTP550 was treated with T4 DNA polymerase and dNTPs, ligated to NotI linkers, cut with Not I, and ligated to the NotI site in pKM201. Temperature-sensitive red-gam and lacI expressing plasmid; Amp R.

TABLE 1

Strains used and constructed in this study

| Strain | Description | Source or reference |
|---|---|---|
| EDL933 | EHEC O157:H7 prototype | Riley et al (1983) |
| TUV93-0 | Stx-derivative of EDL933 | A. Donohue-Rolfe |
| JPN15/pMAR7 | Amp$^R$ derivative of EPEC E2348/69 O127:H6 prototype | Jerse et al (1990) |
| | Derivatives of EHEC TUV93-0: | |
| KM45 | Δtir-cesT-eae::cat | TUV93-0/pTP223 × SacI-SphI fragment from pKM185 |
| KM46 | Δtir-cesT-eae::cat-sacB | TUV93-0/pTP223 × SacI-SphI fragment from pKM188 |
| KM47 | Δeae::cat | TUV93-0/pTP223 × SacI-SphI fragment from pKM184 |
| KM48 | Δeae::cat-sacB | TUV93-0/pTP223 × SacI-SphI fragment from pKM187 |
| KM60 | Δeae | KM48/pTP223 × SacI-SphI fragment from pKM181 |
| KM61 | Δtir-cesT-eae | KM46/pTP223 × SacI-SphI fragment from pKM182 |
| KC2 | Δtir::cat | TUV93-0/pTP223 × KpnI fragment from pKC2 |
| KC3 | Δtir::cat-sacB | TUV93-0/pTP223 × KpnI fragment from pKC3 |
| KC5 | Δtir | KC3/pTP223 × KpnI fragment from pKC5 |
| KC27 | Δtir::cat | TUV93-0/pKM201 × PCR fragment (5KO-H-tir, 3KO-H-tir) |
| KC30 | ΔLEE::cat | TUV93-0/pKM201 × PCR fragment (5KO-H-LEE, 3KO-H-LEE) |
| KC40 | ΔespF::cat | TUV93-0/pKM201 × PCR fragment (5KO-H-espF, 3KO-H-espF) |
| KM90 | ΔlacZ::cat | TUV93-O/pKM201 × PCR fragment (cat13, cat14) |

TABLE 1-continued

Strains used and constructed in this study

| Strain | Description | Source or reference |
|---|---|---|
| KM94 | ΔlacZ::kan | TUV93-O/pKM208 × PCR fragment (kan3, kan4) |
| KM95 | ΔeaeH::kan | TUV93-O/pKM208 × PCR fragment (5KO-H-Island 12, 3KO-H-Island 12) |
| KM96 | ΔZ3025-Z3026::kan | TUV93-O/pKM208 × PCR fragment (5KO-H-Island 77, 3KO-H-Island 77) |
| KM97 | ΔZ3664::kan | TUV93-O/pKM208 × PCR fragment (5KO-H-Island 103, 3KO-H-Island 103) |
| KM98 | ΔhopD-Z4695-yheA::kan | TUV93-O/pKM208 × PCR fragment (5KO-H-Island 130-131, 3KO-H-Island 130-131) |
| KM99 | ΔZ58155-Z5816::kan | TUV93-O/pKM208 × PCR fragment (5KO-H-Island 169, 3KO-H-Island 169) |
| | Derivatives of EPEC JPN15/pMAR7 | |
| KC21 | ΔLEE::cat | JPN15/pMAR7/pTP223 × PCR fragment (3KO-P-LEE, 5KO-P-LEE) |

TABLE 2

Plasmids constructed for this study pKC2 Regions upstream and downstream of EHEC tir, generated by PCR using primer pairs H-TirU/H-TirN and H-TirC/H-TirD, respectively, were fused in a second stage PCR reaction to the cat gene from pTP883 to generate a Δtir::cat DNA fragment, which was cut with KpnI and ligated to the KpnI site of pUC19 (Δtir::cat plasmid).

pKC3 The NotI fragment containing cat-sacB from pKM154 was ligated to the NotI site of pKC2 (Δtir::cat-sacB plasmid).

pKC5 pKC2 was digestedwith NotI and the backbone was religated, generating an EHEC fragment which replaces codons 24-543 of tir with the NotI-containing sequence GCGGCCGCG (in-frame Δtir plasmid).

pKM181 The PCR product containing the 1.5 kb region upstream of eae, generated by primers pairs EaeU/EaeN, was digested with SacI and NotI and ligated to the SacI-NotI fragment from pKM182, containing the 1.5 kb downstream region of eae, generating an EHEC fragment which replaces codons 4-932 of eae with the NotI-containing sequence GCGGCCGCA (in-frame Δeae plasmid).

pKM182 The 1.5 kb regions upstream and downstream of the EHEC tir-cesT-eae region were generated by PCR using primers pairs TirU/TirN and EaeC/EaeD, respectively. The upstream fragment was cut with SacI and NotI and the downstream fragment was cut with SphI and NotI. These fragments were cloned in a 3-piece ligation into the SacI-SphI backbone of pUC19, generating an EHEC fragment that fuses codon 3 of tir to codon 933 of eae via an in-frame NotI-containing sequence GCGGCCGCA (in-frame Δtir-cesT-eae plasmid).

pKM184 The ApaI-NheI cat-containing fragment from pTP826 was treated with T4 polymerase and dNTPs, ligated to NotI linkers, cut with NotI, and ligated to the NotI site of pKM181 (Δeae::cat plasmid).

pKM185 The ApaI-NheI cat-containing fragment from pTP826 was treated with T4 polymerase and dNTPs, ligated to NotI linkers, cut with NotI, and ligated to the NotI site of pKM182 (Δtir-cesT-eae::cat plasmid)

pKM187 The NotI fragment containing cat-sacB from pKM154 was ligated to the NotI site of pKM181 (Δeae::cat sacB plasmid).

pKM188 The NotI fragment containing cat-sacB from pKM154 was ligated to the NotI site of pKM182 (Δtir-cesT-eae::cat sacB plasmid).

pKM200 The BglII fragment from pTP806, containing Ptac-gam-red, was ligated to the BamHI site in pMAK705. Temperature-sensitive red-gam expressing plasmid; $Cam^R$.

pKM201 The BglII fragment from pTP806, containing Ptac-gam-red, was ligated to the BamHI site in pAMPts. Temperature-sensitive red-gam expressing plasmid; $Amp^R$.

pKM208 The EcoR-PstI lacI-containing fragment from pTP550 was treated with T4 DNA polymerase and dNTPs, ligated to NotI linkers, cut with NotI, and ligated to the NotI site of pKM201. Temperature-sensitive red-gam and lacI expressing plasmid; $Amp^R$.

TABLE 3

Primers used for this study

Generation of long homology plasmid substrates.

TirU
ATCATCGAGCTCACCGAGCAGTTCTCGATTGCT  (SEQ ID NO: 1)
ATT (SacI)

TirN
TTAGACGAATGCGGCCGCAATAGGCATAAATAT  (SEQ ID NO: 2)
CTCCTTTTT (NotI)

TirC
ATGCCTATTGCGGCCGCATTCGTCTAAATATAT  (SEQ ID NO: 3)
CCATAATCA (NotI)

TirD
ATCATCGCATGCCACCAGAAAAATCCTGATCAA  (SEQ ID NO: 4)
TGA (SphI)

EaeU
ATCATCGAGCTCGGAAATGCGATTCCGTCA  (SEQ ID NO: 5)
(SacI)

EaeN
TTATTCTACTGCGGCCGCAGTAATCATGTTATG  (SEQ ID NO: 6)
GCTCCACCA

EaeC
ATGATTACTGCGGCCGCAGTAGAATAATTCCAT  (SEQ ID NO: 7)
AACCACCCC (NotI)

EaeD
ATCATCGCATGCTAAAACTTCTCAATGGTGCGA  (SEQ ID NO: 8)
TGC (SphI)

H-tirU
ATCATCGGTACCGCACGTCAGTTTGCTCTTCAA  (SEQ ID NO: 9)
GAG (KpnI)

H-tirN
TGCCGATCAACGTCTCATGCGGCCGCAGGTAAT  (SEQ ID NO: 10)
GGAGGTGCAGGAGGAAT (NotI)

H-tirC
AATGGCAGAAATTCGAAAGCGGCCGCGAATACT  (SEQ ID NO: 11)
TCGAATAACCCACCAGC (NotI)

H-tirD
TCATCAGGTACCTCGGTCATGTTGCTTTTGGTC  (SEQ ID NO: 12)
ACG (KpnI)

Generation of PCR substrates for one-step gene deletion:

5KO-H-lacZ
GACGGGTTGTTACTCGCTCACATTTAATGTTGA  (SEQ ID NO: 13)
TGAAAGCGCGGCCGCATGAGACGTTGA 3KO-H-lacZ
AAGAAAGCCTGACTGGCGGTTAAATTGCCAACG  (SEQ ID NO: 14)
CTTATTAGCGGCCGCTTTCGAATTTCT 5KO-H-EspF
ATGCTTAATGGAATTAGTAACGCTGCTTCTACA  (SEQ ID NO: 15)
CTAGGGCGGCAGCTTGTAGCGGCCGCATGAGAC
GTTGAT 3KO-H-EspF
TTACCCTTTCTTCGATTGCTCATAGGCAGCTAA  (SEQ ID NO: 16)
ATGATCTTTTAATGCCTG GCGGCCGCTTTCGA
ATTTCTGC 5KO-H-tir
ATGCCTATTGGTAATCTTGGTCATAATCCCAAT  (SEQ ID NO: 17)
GTGAATAATTCAATTCCTCCTGCACCTC GCGG
CCGCATGAGACGTTGA 3KO-H-tir
GATATATTTAGACGAAACGATGGGATCCCGGCG  (SEQ ID NO: 18)
CTGGTGGGTTATTCGAAGTATTCACA GCGGCC
GCTTTCGAATTTCT

Generation of PCR substrates for one-step island deletion:

5KO-H-LEE
TTTCTGTTATCATTACTGCCAATATTTGTTGTT  (SEQ ID NO: 19)
ATTGGTACTTCATTCCTGAAAGCGGCCGCATGA
GACGTTGAT

3KO-H-LEE
AAAGCTGTCGAAATATTAATCGCGATAATGATA  (SEQ ID NO: 20)
TCCACCACAACTGTTGGTAGTGCGGCCGCTTTC
GAATTTCTGC

5KO-P-LEE
AAGTATTTTATTGAATTCATTTAAAGATAATTA  (SEQ ID NO: 21)
TCTTAGCATTATTCAGGCGGCCGCATGAGACGT
TGAT

3KO-P-LEE
TGTTCTTCTGATATCCAGAAACGCCCCTCATAG  (SEQ ID NO: 22)
CCCGAGTATGTCAACGTGCGGCCGCTTTCGAAT
TTCTGC

ΔIsland 12A
CTGACACTGAGCGCCGGGCATAAGCAGGGCAAG  (SEQ ID NO: 23)
AGCGGTGAATCTCTGATGTTACATTGC ΔIsland 12B
CCTCTTTCCGCTATGAAGGTGAGTGGGAGCACT  (SEQ ID NO: 24)
ACCCTGATTCAACTCAGCAAAAGTTCG ΔIsland 77A
AGCCAGGTCAACAGGTCAGTATGGGAAGGCGAA  (SEQ ID NO: 25)
CAACTCGAATCTCTGATGTTACATTGC ΔIsland 77B TABLE 3-continued Primers used for this study

```
TGTTGTTAATGACATCCGATCTCACCGCGTGGG    (SEQ ID NO: 26)

GCATGGATTCAACTCAGCAAAAGTTCG

ΔIsland 103A
TTGACATCCTCCACGCCCTGAATGACGAGGATC    (SEQ ID NO: 27)

CCTGCTAAATCTCTGATGTTACATTGC

ΔIsland 103B
GGTGCGCCGTAAAACCCCGTCCTTCAGGGCGGG    (SEQ ID NO: 28)

GATATAATTCAACTCAGCAAAAGTTCG

ΔIsland 130-131A
GCAAATCTGAGCCTGACGCAAGCATCGGGCAGA    (SEQ ID NO: 29)

AATTAATAATCTCTGATGTTACATTGC

ΔIsland 130-131B
TGCCCGTAATTTGAGCTCGAAATATTTAGTCGT    (SEQ ID NO: 30)

AATTTTGTTCAACTCAGCAAAAGTTCG

ΔIsland 169A
CCGGTGCGCCGTAAAACCCCGTCCTTCAGGGCG    (SEQ ID NO: 31)

GGGATATAATCTCTGATGTTACATTGC

ΔIsland 169B
TTGACATCCTCCAAGCCCTGAAGGACGTGGATC    (SEQ ID NO: 32)

CCTGCTATTCAACTCAGCAAAAGTTCG

ΔIsland 169E
CCGGTGCGCCGTAAAACCCCGTCCTTCAGGGCG    (SEQ ID NO: 33)

GGGATATTTCAACTCAGCAAAAGTTCG

ΔIsland 169F
TTGACATCCTCCAAGCCCTGAAGGACGTGGATC    (SEQ ID NO: 34)

CCTGCTAAATCTCTGATGTTACATTGC
```

B. Electroporation and Gene Replacement Protocol

A single fresh colony of EHEC or EPEC was placed into 20 ml of LB plus 15 µg ml$^{-1}$ tetracycline (for pTP223) or 100 µg ml$^{-1}$ ampicillin (for pKM201 and pKM208) and shaken at 30° C. in an 125 ml flask. At ~10$^7$ cells/ml, IPTG was added to a final concentration of 1 mM. When the culture reached a density of 0.5-1×10$^8$, the cells were heat shocked for 15 minutes by swirling at 42° C., transferred to an ice-water bath for 10 min with swirling, then collected by centrifugation. The cells were resuspended in 1 ml of ice-cold 20% glycerol—1 mM MOPS (unbuffered), transferred to a 1.5 ml sterile eppendorf tube, and spun in a microfuge for 30 seconds (moderate speed). The supernatant was removed; the cells were resuspended in the same buffer and recentrifuged. This step was repeated and the cells were finally resuspended in 90-100 µl of ice-cold 20% glycerol—1 mM MOPS.

Electroporation cuvettes (Biorad) were cooled in an ice-water bath for at least 10 minutes prior to use. DNA samples contained either 0.1-0.5 µg of purified DNA fragments or 0.2-10.0 µg of plasmid digests in TE or water. A 50 µl sample of cells was mixed with 1-5 µl of DNA, transferred to the electroporation cuvette, and incubated on ice for 1 minute. The cuvette was thoroughly but quickly dried and the cells were shocked as described previously (Murphy, 1998). Following electroporation, the cells were recovered by suspension in 0.3 ml LB, diluted in 2.7 ml LB, grown by rolling at 37° for 1.5 hour, and plated on LB plates containing either 10-15 µg ml$^{-1}$ chloramphenicol or 20 µg ml$^{-1}$ kanamycin. (Growing for less that one hour with kanamycin markers drastically reduced the recovery of recombinants). Alternatively, though usually not required, the cell cultures were grown overnight before plating. After overnight growth, drug-resistant transformants of EHEC and EPEC were restreaked on LB plates containing the appropriate drug.

In some of the early experiments, ice-cold water was used instead of 20% glycerol—1 mM MOPS for resuspending the cells. However, it was found that the glycerol/MOPS buffer improved the electroporation survivor rate for EHEC (and thus recovery of recombinants), as was reported for electroporation of *Pseudomonas aeruginosa* (Farinha and Kropinski, 1990). In some experiments, transformants were also checked for tetracycline (pTP223) or ampicillin (pKM201 and pKM208) sensitivity indicating loss of the Red-producing plasmid (if desired). These Red-producing plasmids were lost spontaneously at relatively high frequency following growth and electroporation, i.e., selection at 42 degrees for loss of the temp-sensitive pKM208 replicon was usually not required. Various numbers of transformants that successfully restreaked on to fresh drug plates were analyzed by PCR to verify chromosomal replacement of the target gene(s), as described in FIG. 1. The selection for Suc$^R$-Cam$^R$ transformants (containing precise in-frame deletions) was done as described previously for *E. coli* K-12 (Murphy et al., 2000).

C. Infections and Immunoflourescence Microscopy

HeLa cells were cultured in DMEM plus 10% fetal bovine serum, 100 U ml$^{-1}$ penicillin, 100 µg ml$^{-1}$ streptomycin, and 2 mM L-glutamine at 37° C. in 5% CO$_2$. Prior to infections, EPEC were cultured in DMEM+100 mM HEPES pH 7.4 in 5% CO$_2$, growth conditions previously shown to maximize type III secretion. HeLa cells grown on 12 mm glass coverslips were infected in DMEM plus 3% fetal bovine serum, 20 mM HEPES pH 7.4, and 2 mM L-glutamine at 37° C. in 5% CO$_2$ for five hours and processed as described previously (Campellone et al., 2002). Monolayers were stained with a 1:500 dilution of anti-HA mAB HA.11 (Covance) for 30 minutes followed by an additional 30 minute staining with 1 µg ml$^{-1}$ TRITC-phalloidin (Sigma), 1 µg ml$^{-1}$ DAPI, and a 1:200 dilution of Alexa488-conjugated goat anti-mouse IgG (Molecular Probes).

D. Infections and Immunoblotting

HeLa cells and bacteria were cultured as described above. 90% confluent HeLa cell monolayers grown in 6-well plates were infected with approximately 10$^8$ EPEC per well for 3.5 hours. Bacteria were then washed 3 times with PBS, killed by treatment for an additional 0.75 hours with 50 µg ml$^{-1}$ gentamicin in infection media, and washed 5 times with PBS. Cells were collected by treatment with PBS+2 mM EDTA, washed once with PBS, lysed in lysis buffer (50 mM HEPES pH 7.4, 50 mM NaCl, 1 mM Na$_3$VO$_4$, 10 µg ml$^{-1}$ peptstatin, 10 µg ml$^{-1}$ aprotinin, 10 µg ml$^{-1}$ leupeptin, and 100 µg ml$^{-1}$ PMSF) and processed for western blotting. Infected HeLa lysate samples were boiled in SDS-PAGE loading buffer, electrophoresed, and transferred to PVDF membranes. The membranes were probed with anti-HA antiserum (1:1000) as described previously (Campellone, et al., 2002). N-WASP and OmpA served as loading controls for cells and bacteria, respectively, and were stained with rabbit anti-rat N-WASP antiserum (1:1000) and anti-OmpA antiserum (1:1000) and visualized with alkaline-phosphatase conjugated anti-rabbit antiserum.

Introduction to Examples 1-7

Pathogenic *E. coli* species should be amenable to the use of λ Red for chromosomal engineering. Enterohemorrhagic *E. coli* O157:H7 (EHEC) and enteropathogenic *E. coli* (EPEC) are members of the attaching and effacing (AE) family of enteric pathogens [21, 22]. These pathogens bind tightly to the intestinal epithelium and cause localized effacement of micovilli, followed by alteration of the cytoskeleton beneath sites of bacterial attachment. Some labs have used λ Red to promote gene knockouts in EPEC by recombination between linear plasmid DNA fragments containing long regions of homology (~0.5-1 kb) and the EPEC chromosome [23-25]. In addition, a few reports have utilized PCR substrates containing short regions of homology to perform gene replacement in EHEC [26-28], the latter report employing plasmids and protocols described herein. None of these reports, however, described the frequency of recombinant formation or the reproducibility of Red-promoted PCR-mediated recombination in EHEC at multiple loci. Indeed, initial attempts by the instant inventors to employ λ Red for PCR-mediated gene replacement at various loci in EHEC in EPEC were met with sporadic success, similar to the limited success seen with Red-promoted short homology recombination in *Y. pseudotuberculosis*. These difficulties prompted the inventors to examine more closely the methodologies of λ Red promoted PCR-mediated gene replacement, especially in regard to optimizing its use in EHEC and EPEC.

Examples 1-7 demonstrate that expression of bacteriophage λ red and gam recombination functions in enterohemorrhagic *E. coli* O157:H7 (EHEC) and enteropathogenic *E. coli* (EPEC) promotes efficient recombination with linear DNA substrates in these pathogens. This technology has been used to generate marked and unmarked deletions of known virulence genes eae (intimin) and tir (translocated intimin receptor). In addition, several EHEC/EPEC tir hybrids have been crossed onto the EPEC chromosome at the endogenous tir locus. A hybrid Tir that contains an EPEC-Tir derived Nck-binding site in the context of an otherwise EHEC Tir promoted wild type looking pedestals when overexpressed from a low-copy number plasmid, but formed extended pedestals when expressed at normal levels from its chromosomal location. The suppression of this phenotype when this Tir molecule is expressed from a low copy number plasmid highlights the utility of a genetic technique that allows one to express mutant genes from their chromosomal locations. Finally, using the λ Red system, five O157-specific islands (O-islands) of EHEC were easily and precisely deleted from the chromosome by electroporation with PCR-generated substrates containing drug markers flanked with 40 bp of target DNA. PCR-mediated λ Red-promoted recombination was also successful in EPEC.

The instant inventors have found conditions that allowed PCR-mediated recombinants to be reproducibly obtained using λ Red recombination in EHEC and EPEC, guidelines that can be applied to the use of Red in other pathogenic bacteria. These steps include the use of an optimal buffer for the preparation of electrocompetent cells, a heat-shock step that induces higher frequencies of gene replacement, and proper positioning of the drug marker within the recombinant PCR substrate. As demonstration of the utility of this technology, five EHEC O-islands were easily deleted from the EHEC chromosome by simple electroporation with PCR-generated substrates. The importance of limiting expression of Red functions during growth of EHEC was noted, as extended expression of the recombination functions induces a 10-fold increase in spontaneous mutagenesis. Gene replacement frequencies generated by various treatments of plasmid substrates to construct marked and precise deletions of EHEC eae, tir, and the eae-cesT-tir operon, are presented.

Example 1

Red-mediated Recombination in Pathogenic Bacteria Using Long Homology Recombination (LHR) Substrates (1-2 kb)

The present inventor has previously shown that the multicopy plasmid pTP223 supports λ Red-mediated recombination with long substrates (drug markers flanked by ~1 kb of target DNA; Murphy, 1998; Murphy et al., 2000). This plasmid expresses both λ Red and the anti-RecBCD function, Gam, under control of the Plac promoter, as well as the lacI repressor gene from its own promoter (Poteete and Fenton, 1984). Plasmid substrates were constructed that contained the cat gene (conferring resistance to chloramphenicol) flanked by upstream and downstream regions of tir, eae, or the tir-cesT-eae operon (cesT encodes a chaperone for Tir). Linear DNA recombination substrates (i.e., the cat gene flanked by 1.5 kb of target DNA) were generated from these plasmids by digestion with restriction enzymes (see FIG. 1A and Tables 1 & 2 for details). EHEC cells harboring pTP223 were electroporated with the restriction digests, or gel-purified linear fragments containing the marked deletions, and plated on LB plates containing chloramphenicol. Among the chloramphenicol resistant colonies, potential chromosomal substitutions were distinguished from simple plasmid transformants by their sensitivity to ampicillin (bla gene carried within the pUC19 plasmid backbone). Results of a number of these experiments are shown in Table 4.

In all cases, Δeae, Δtir, or Δeae-cesT-tir was easily generated with these plasmid substrates, generating as few as 2 and as many as 1000 gene replacements per experiment, depending on the nature and amount of the transforming DNA. These genes were replaced with either the cat drug marker (Table 4, lines 1, 2, 4-9) or a cat-sacB cassette (Table 4, lines 3, 10 and 11). The latter substitutions generated strains that were subsequently used to generate in-frame, precise deletions (see Table 5). All gene replacements were verified by PCR analysis (as described in FIG. 1—data not shown). Overall, the following observations were evident. Electroporation of simple plasmid digests resulted in a high number of plasmid transformants (i.e., $Cam^R$-$Amp^R$, see Table 4, lines 1-3), due to incomplete digestion or religation of the plasmid substrate in vivo. A higher number of potential gene replacement transformants (i.e., $Cam^R$-$Amp^S$ colonies) could be obtained by further digestion of the plasmid with a backbone-specific restriction enzyme, ApaLI (see Table 4, lines 4-7), or by gel purification of the linear DNA recombination substrate (Table 4, lines 8-11).

Surprisingly, the Red-producing plasmid pTP223 is spontaneously lost during this process (between 10-50% of the transformants are $Tet^S$). Thus, a separate step to cure the recombinant of the Red plasmid is not required. These experiments show that marked and precise deletions can be easily generated in EHEC without the need to form and resolve plasmid co-integrates. This procedure can likewise be used to generate deletions, for example, at the recC and dam loci in EHEC.

TABLE 4

Gene replacements in the tir-cesT-eae region of enterohemorrhagic
E. coli 0157:H7 using long homology-containing substrates

| Exp # | Substrate preparation | Amount of DNA | Genotype of linear fragment | Total Transformants | Percent transformants Amp sensitive | Recombinants verified by PCR (# verified/# tested) |
|---|---|---|---|---|---|---|
| | Plasmid digests: | | | | | |
| 1. | restriction digest pKM184 (SacI, SphI) | 2 μg | Δeae::cat | >500 | 11% (4/35) | 1/1 |
| 2. | restriction digest pKM185 (SacI, SphI) | 2 μg | Δeae-cesT-tir::cat | 103 | 2.6% (2/76) | 1/1 |
| 3. | restriction digest pKM 187 (SacI, SphI) | 1 μg | Δeae::cat sacB | >500 | 2.8% (1/35) | 1/1 |
| | Plasmid digests including backbone: | | | | | |
| 4. | restriction digest pKM184 (SacI, SphI, ApaLI) | 0.5 μg | Δeae::cat | 52 | 57% (4/7) | NT |
| 5. | restriction digest pKM184 (SacI, SphI, ApaLI) | 10 μg | Δeae::cat | >500 | 95% (143/151) | 10/10 |
| 6. | restriction digest pKM185 (SacI, SphI, ApaLI) | 2 μg | Δeae-cesT-tir::cat | 30 | 56% (9/16) | 9/10 |
| 7. | restriction digest pKM185 (SacI, SphI, ApaLI) | 2 μg | Δeae-cesT-tir::cat | 36 | 50% (9/18) | 7/9 |
| | Gel-purified fragments: | | | | | |
| 8. | purified SacI-SphI fragment from pKM185 | 0.5 μg | Δeae-cesT-tir::cat | 225 | 100% (20/20) | 1/1 |
| 9. | purified KpnI fragment from pKC2 | 0.1 μg | Δ tir::cat | 6 | NT | 6/6 |
| 10. | purified SacI-SphI fragment from pKM188 | 0.6 μg | Δ eae cesT tir::cat sacB | 273 | 100% (40/40) | 1/1 |
| 11. | purified KpnI fragment from pKC3 | 0.05 μg | Δtir::cat sacB | 2 | NT | 2/2 |

TABLE 5

Generation of EHEC 0157:H7 unmarked deletions of eae and tir

| Exp | Substrate Preparation | Amount of DNA | Genotype of linear fragment | Genotype of recipient | Percent $Suc^R Cam^S$ transformants[a] | Recombinants verified by PCR (# verified/# tested) |
|---|---|---|---|---|---|---|
| 1. | Digest of pKM182 (SacI, SphI) | 2 μg | Δeae-cesT-tir | Δeae-cest-tir::cat-sacB | 94% (94/100) | 6/6 |
| 2. | Digest of pKM181 (SacI, SphI) | 2 μg | Δeae | Δeae::cat-sacB | 88% (88/100) | 6/7 |
| 3. | Purified KpnI fragment from pKC5 | 0.1 μg | Δtir | Δtir::cat-sacB | 10.5% (2/19) | 2/2 |

[a]The selection for $Suc^R$-$Cam^S$ transformants (containing precise in-frame deletions) was performed as described previously for E. coli K-12 (Murphy et al, 2000).

Example 2

Red-mediated Recombination does not Compromise Infectious Processes of the Pathogenic Bacteria EHEC and EPEC To determine if Red-mediated recombination induced any deleterious effects on EPEC or EHEC strains, the abilities of several strains to form actin pedestals on cultured mammalian cells were tested. Strains EHECΔtir and EPECΔtir (KC5 and KC14, respectively) were generated by Red-mediated recombination using pTP223 (see Table 1). As expected, due to the requirement of Tir in actin signaling, neither of these strains formed pedestals on infected HeLa cells, but were capable of being functionally complemented for pedestal formation by plasmid encoded Tir (Campellone, et al., 2002). These results indicate that no obvious ectopic mutations arose in these two different Red-treated strains to prevent the highly coordinated tasks of bacterial binding and type III translocation of effector proteins.

Example 3

Benefits of Using Red-mediated Recombination in Functional Genomics Applications This Example demonstrates at least one benefit of expressing proteins (e.g., mutant proteins) from a chromosomal location versus overexpressing from a plasmid. In this Example, it is first demonstrated that proteins are expressed at lower (i.e., normal) levels when expressed from a chromosomal location, as compared to artificially high levels expressed from a comparable plasmid. Expression at normal levels unmasked a mutant phenotype that was not observed in the overexpression situation. It appears that overexpression of mutant protein rescued, and thus masked, the mutant phenotype. This experiment demonstrates the benefit of expressing mutant proteins at a normal level (i.e., from a chromosomal location) when performing functional genomics studies.

Expression Levels and Translocation into Host Cells of Proteins Expressed from a Chromosomal Location as Compared to Plasmid-Expressed Proteins One advantage of being able to couple the efficiency of Red-mediated recombination with the counterselectable marker sacB is the ability to cross DNA fragments containing molecular alterations onto endogenous chromosomal loci. These mutants can then be tested for function when expressed at normal levels, thereby avoiding any potential plasmid-borne overexpression artifacts.

Figure 2A:
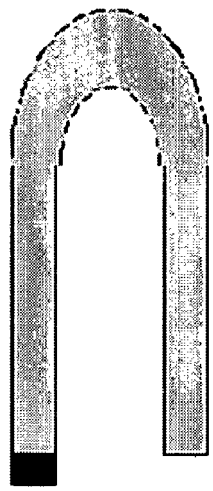
Figure 2A:
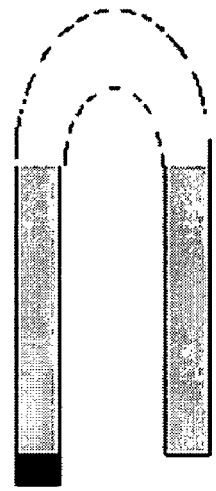
Figure 2A:
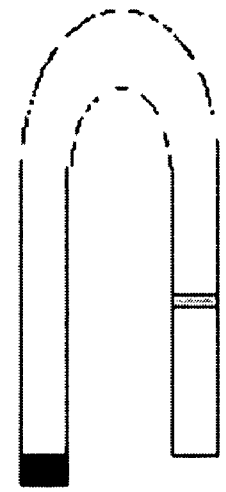

Recently, several laboratories have observed that the EHEC Tir molecule does not function for actin pedestal formation when expressed in EPEC (Campellone, et al., 2002; DeVinney, et al., 1999; Kenny, 2001). A twelve amino acid sequence of the EPEC Tir molecule required for actin signaling and binding to the host adaptor protein Nck was identified in the context of plasmid-derived EHEC/EPEC Tir chimeras expressed in an EPEC strain harboring EHEC intimin (Campellone, et al., 2002). The plasmid-derived expression levels of some of these Tir molecules was compared with identical Tirs which were crossed onto the EPEC chromosome (via Red-mediated recombination). In particular, HA-tagged wild type EPEC Tir (Tir-PPP) and two EHEC/EPEC Tir chimeras (FIG. 2A) were examined for levels of Tir expression and translocation into host cells. One chimera possessed the N- and C-terminal cytoplasmic domains of EPEC Tir with the central extracellular (intimin-binding) domain of EHEC Tir (Tir-PHP), and one was entirely composed of EHEC Tir with the exception of an EPEC-Tir derived Nck-binding site (NBS) incorporated into its C-terminal cytoplasmic domain (Tir-HHH$_{NBS}$) (FIG. 2A). HeLa cell monolayers were infected with EPEC strains expressing these three versions of Tir either from the endogenous Tir locus or from a low copy plasmid, with expression driven by an identical EPEC Tir promoter in each case. Non-intimately associated bacteria were killed with gentamicin, and the remaining infected HeLa cells were collected, processed for SDS-PAGE, and immunoblotted for Tir. Tir residing in the bacterial cytoplasm typically migrates at approximately 78 kDa, while Tir which has been translocated into host cells is modified by serine/threonine phosphorylation and migrates at 90 kDa (DeVinney, et al., 1999; Kenny et al., 1997).

Figure 2B:
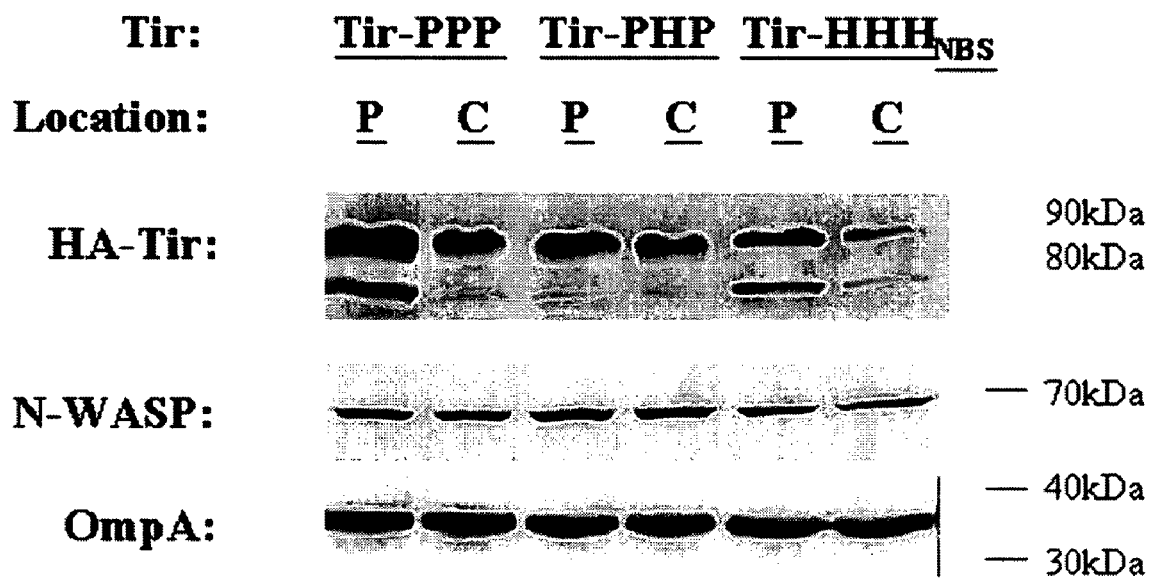

Examination of Tir immunoblots indicated that for each of the three Tir molecules examined, the bacterially-associated 78 kDa form was expressed at higher levels when encoded on a low copy number plasmid (FIG. 2B). Similarly, strains expressing Tir from plasmids translocated more Tir into mammalian cells, as evidenced by increases in levels of the ~90 kDa form of Tir (FIG. 2B).

Chromosomal Expression of a Mutant Gene (the EHEC/EPEC Tir Chimera) Reveals a Mutant Phenotype (The Long-Pedestal Phenotype)

Figure 3A:
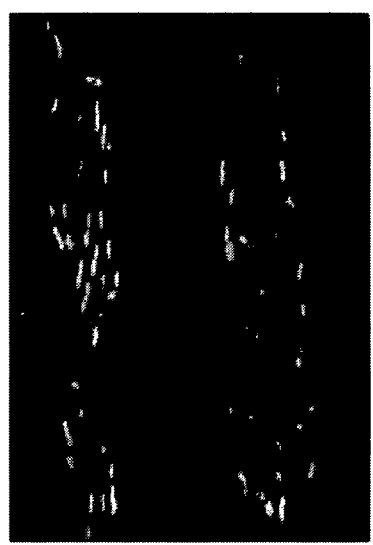
Figure 3A:
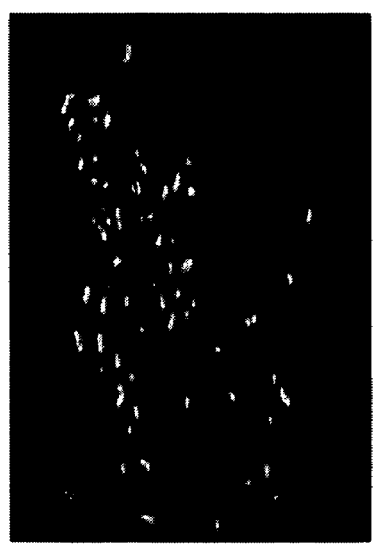
Figure 3A:
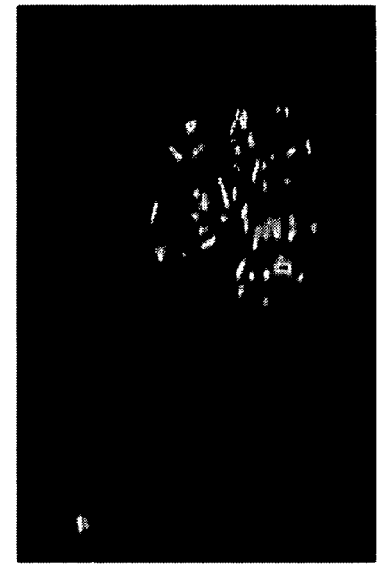
Figure 3B:
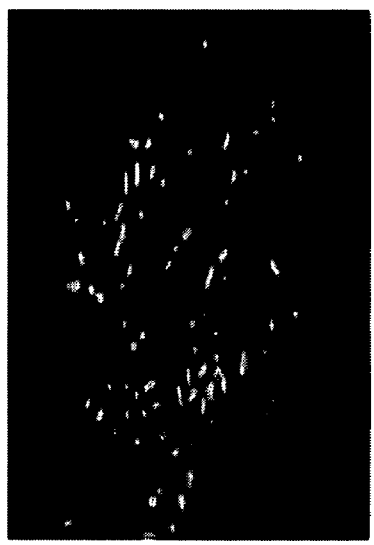
Figure 3B:
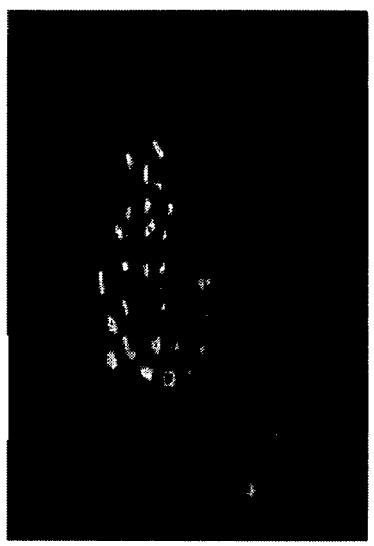
Figure 3B:
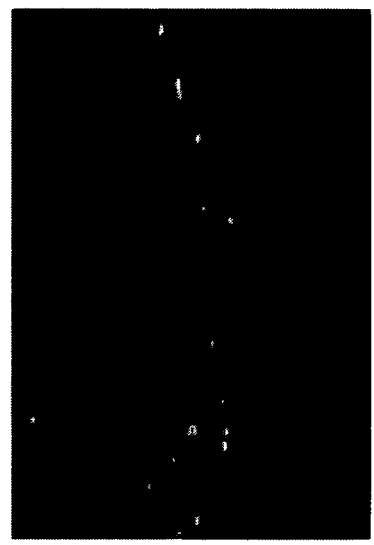

To determine whether these differences in expression and translocation levels of Tir had any consequences on actin signaling and pedestal formation, EPEC strains expressing Tir-PPP, Tir-PHP, or Tir-HHH$_{NBS}$ were examined for differences in pedestal structures. Wild type EPEC Tir-PPP and chimeric Tir-PHP exhibited similar pedestal formations whether they were delivered at endogenous chromosomal levels or at higher plasmid-driven levels (FIG. 3A-B). In contrast, chimeric Tir-HHH$_{NBS}$, which contains EPEC Tir Nck-binding site incorporated into an otherwise EHEC Tir, displayed striking morphological differences in pedestals depending upon the location of the tir gene. EPEC delivering higher levels of Tir-HHH$_{NBS}$ due to plasmid-derived expression generally formed pedestals similar to bacteria expressing wild type EPEC Tir (FIG. 3A). But upon close inspection, a small percentage of these bacteria formed pedestals which appeared to be increased in length (data not shown). However, when Tir-HHH$_{NBS}$ was expressed from its chromosomal locus, bacteria generated a large number of pedestals of increased lengths (FIG. 3B).

These results suggest that chimeric Tir-HHH$_{NBS}$ is partially defective for pedestal formation, since the morphologies of these pedestals are radically different from wild type (shorter) pedestals, and that this defect can be overcome by overexpression of the chimera. The difference in pedestal formation associated with this Tir chimera can likely be attributed to differences in the N- or C-terminal cytoplasmic domains of the EHEC and EPEC Tir homologues, since chimeric Tir-PHP (which has the EPEC Tir cytoplasmic domains) forms pedestals of normal appearance on HeLa cells (FIG. 3A-B).

Example 4

Red-mediated Recombination in Pathogenic Bacteria Using Short Homology Recombination (SHR) Substrates (40-60 bp of Homology)

Red-promoted gene replacement with the long homology substrates described above required cloning of the marked deletions or substitutions. Despite this restriction, this method of chomosomal engineering can be useful in certain situations (see above, and Discussion). However, a simpler method of generating gene knock-outs in *E. coli* K-12 (and *Salmonella* strains) involves electroporation of PCR products containing short regions (40 bp) of flanking homology to the target gene into λ Red and Gam-producing bacteria. This strategy has been shown to promote high efficiency gene replacement with such substrates in *E. coli* K-12 (Datsenko and Wanner, 2000; Yu et al., 2000) as well as *Salmonella enterica* (see Introduction). Typically, PCR is performed with two primers (60 mers) which contain 20 bases at the 3' ends to amplify a drug marker. In addition, the primers contain 40 bases at the 5' ends that are complimentary to either the N or C-terminal regions of the target gene (see FIG. 1B). The PCR product, which has the drug marker flanked by 40 bases upstream and downstream of the targeted gene of interest, is simply electroporated into Red+Gam producing *E. coli* or *Salmonella*.

While pTP223 promotes gene replacement efficiently with substrates containing long regions of homology to the target gene (Murphy, 1998), PCR substrates containing short regions of homology (40 bp) recombine at very low frequency [Datsenko, 2000 #20; Murphy, unpublished observations]. It has been noted that expression of red from the chromosome, or low copy number plasmids, is better suited for Red-mediated recombination relative to multi-copy plasmids (Murphy, 1998; Datsenko and Wanner, 2000; Yu et aL, 2000). It is assumed that since Red induces the rolling circle mode of replication in medium or high copy number plasmids (Poteete et al., 1988), linear multimers of the plasmid are generated that may compete with the electroporated substrates for the Red recombination functions. This reasoning explains why pTP223, while expressing high levels of Red and Gam, is not optimal for Red-promoted gene replacement in *E. coli* K-12 (especially with short homology substrates).

In contrast, studies by the instant inventor with ΔrecBCD::gam-red chromosomal substitutions (expressing red from either $P_{lac}$ or the stronger $P_{tac}$ promoter) have shown that Red-promoted recombination with short-homology substrates requires higher level expression of the red functions relative to long-homology substrates (unpublished observations). A construct that meets both these requirements (high expression from a single or low copy number replisome) is plasmid pKD46, described by Datsenko and Wanner (Datsenko and Wanner, 2000) which uses the pBAD promoter to express red and gam from a low copy number temperature-sensitive replicon. A similar plasmid, pKM201, was constructed except that gam and red are driven by the Ptac promoter. A variation of pKM201 was constructed which expresses the lacI repressor gene (pKM208), in order to keep expression of red and gam under tight control prior to IPTG induction. In anticipation of the requirement to easily remove these plasmids after gene replacement, both plasmids contain temperature-sensitive origins of replication.

EHEC containing pTP223, pKM201, or pKM208 were electroporated with a PCR substrate containing the kan gene flanked by 40 bases of N- and C-terminal regions of the lacZ gene. As expected, plasmid pTP223 was unable to efficiently promote short-homology recombination in EHEC (data not shown; however, see results with EPEC below). On the contrary, low copy number plasmids pKM201 and pKM208 were able to promote short homology recombination in EHEC at the lacZ locus. Recombinants were detected as white $Kan^R$ colonies on LB-kan plates containing X-gal and IPTG. Cells harboring LacI-expressing pKM208 required prior induction with IPTG for efficient recombination (see below); cells containing pKM201 did not require IPTG addition (due to $P_{tac}$ leakiness in the absence of over-expressed LacI).

In five separate experiments, Red expression from pKM208 produced gene replacements at a rate between 70-600 recombinants per $10^8$ cell survivor (total number of recombinants varied from 750-3000). From one of these experiments, ten out of ten white $Kan^R$ transformants tested positive for gene replacement by the PCR method described in FIG. 1B (data not shown). In addition, a PCR fragment containing a lacZ deletion with a cat insertion worked as well as the one described above using kan. It is noteworthy, however, that while the ΔlacZ::kan allele yielded recombinants at a frequency $0.7-6\times 10^{-6}$ per survivor in EHEC containing pKM208, the same PCR fragment in E. coli K-12 containing pKM208 yielded recombinants at a frequency of $10^{-4}$ per survivor (data not shown). The sequences used in targeting ΔlacZ to the E. coli K-12 and EHEC chromosomes are identical. The reason for this lower frequency is not known, but may be due to an EHEC-specific restriction system(s) or lower rates of DNA uptake following electroporation; other possibilities are considered in the Discussion section.

Gene replacements using short homology substrates was also performed in EHEC containing pKM201 at the tir and espF loci within the LEE, though frequencies of gene replacement at these sites (in repeated experiments) were lower than that seen with the lacZ substrate described above, and usually ranged from 0-20 recombinants per $10^8$ survivor. However, this lower frequency of gene replacement at alternative loci relative to lacZ was also observed in E coli K-12 (unpublished observations). Thus, the lacZ region may be a hotspot for gene replacement, perhaps the result of stable expression of the drug marker following integration at this particular locus (see below). Nonetheless, Red-promoted PCR-mediated gene replacement was successful with both tir and espF.

To assess the overall usefulness of Red-promoted PCR-mediated gene replacement in EHEC, five O157-specific islands (O-islands) in the EHEC chromosome were targeted for deletion; these O-islands are not present in E. coli K-12 (Pema et al., 2001). PCR substrates containing the kan gene flanked by 40 base pairs of DNA bordering O-islands #12, #77, #103, #130-131 and #169 (Table 6) were elect into EHEC containing pKM208. These islands were targeted because they occupy different regions of the chromosome, are of moderate size (733-4253 base pairs in length), and encode either putative virulence factors or unknown proteins. In the first attempt, all five islands were successfully deleted (see Table 6), though there was variability in the frequency of island replacement. Deletion of O-islands #130-131 occurred at a frequency similar to that seen with lacZ gene (~100 $kan^R$ transformants per $10^8$ cell survivors), while the others showed rates ranging from 10-50 fold lower. Thus, λ Red is able to promote efficient short homology recombination with the EHEC chromosome, though at a reduced frequency relative to that seen in E. coli K-12.

The islands selected above ranged from 733-4253 base pairs in length. To determine if any restrictions could be placed on the amount of DNA deleted by Red-promoted recombination, a PCR product was generated containing the cat gene flanked by regions upstream and downstream of an internal section of O-island #148, which contains the locus of enterocyte effacement (LEE). Electroporation with this PCR fragment, designed to delete 9 kb of genes encoding the type III secretion apparatus (see Table 1, strain KC30) generated recombinants at a frequency of 20 per $10^8$ survivors, similar to other deletion frequencies. Thus, both small and large regions of the EHEC chromosome can be deleted in one step using Red-mediated recombination (as has been seen with E. coli K-12). Indeed, an additional 15 islands of EHEC of various sizes up to 45 kb have subsequently been deleted in EHEC by Red-promoted PCR-mediated island replacement (Campellone and Leong, unpublished).

TABLE 6

λ Red-promoted PCR-mediated replacement of five targeted EHEC O-islands[a]

| Targeted Island | Sequence numbers[b] | Gene(s) | putative functions | # of colonies[c] (half the culture) | Growth on kanamycin[d] (# $kan^R$/# streaked) | PCR analysis (# verified/ # tested) |
|---|---|---|---|---|---|---|
| O-island #12 | 353934-358187 | eaeH | putative adhesion | 10 | 8/10 | 3/3 |
| O-island #77 | 2710424-2712382 | Z3025 | unknown function | 37 | 10/10 | 4/6 |
| O-island #103 | 3315828-3317575 | Z3664 | putative virulence protein | 18 | 18/18 | 2/3 |
| O-island #130-131 | 4255687-4256420 | hopD | putative enzyme; degradation | 254 | 18/20 | 3/3 |
| | | Z4695 | putative iron storage | | | |
| | | yheA | unknown function | | | |

TABLE 6-continued

λ Red-promoted PCR-mediated replacement of five targeted EHEC O-islands[a]

| Targeted Island | Sequence numbers[b] | Gene(s) | putative functions | # of colonies[c] (half the culture) | Growth on kanamycin[d] (# kan[R]/# streaked) | PCR analysis (# verified/ # tested) |
|---|---|---|---|---|---|---|
| O-island #169 | 5311698-5313445 | Z5815 | putative transposase | 5 | 5/5 | 2/5 |
|  |  | Z5816 | putative virulence protein |  |  |  |

[a]O157::H7 genetic elements not present in E. coli K-12
[b]Genbank accession number AE005174 (Perna et al., 2001)
[c]An estimated 0.25 μg of DNA (3.5 μl) was mixed with 50 μl of electrocompetent EHEC cells and shocked as described in Experimental Procedures. Cells were suspended in 3 ml LB following electroporation and grown at 37° for 90 min. Half the culture (1.5 ml) was concentrated by centrifugation and spread on LB plates containing 20 μg/ml kanamycin. In the same experiment, a PCRfragment containing the ΔlacZ::kan allele generated 272 Kan[R] transformants.
[d]Following 24 h growth, candidates were restreaked on LB-kan plates. Among these Kan[R] candidates, recombinant deletion formation was verified by PCR analysis (as described in FIG. 1B).

Example 5

Drug Marker Context Dependency Affects the Efficiency of Gene Replacement

EHEC strains containing the kan substitutions shown in Table 6 were further purified by streaking on LB plates containing 40 μg/ml$^{-1}$ kanamycin. Interestingly, kan substituted islands #12, #77 and #169, while selected on LB plates containing 20 μg ml$^{-1}$, did not grow at this higher kanamycin concentration (but did restreak well at 20 μg ml$^{-1}$). The other two substitutions (Δisland #103::kan and Δislands #130-131::kan), which consistently gave higher frequencies of gene replacement relative to the others, grew well on LB containing 40 μg ml$^{-1}$ kanamycin. This result suggests that the position and/or orientation of the drug cassette within the chromosome likely alters its expression levels. Thus, the low frequency of O-island #169 replacement (see Table 6) might be due to the influence of neighboring transcripts reading into the kan gene following integration of the Δisland 169::kan PCR substrate into the chromosome, or instability of the kan transcript due to sequences fused to its 3' end.

To test this hypothesis, deletion of O-island #169 was repeated using a PCR product that reversed the direction of kan transcription within this chromosomal region (primers 5KO-H-island169L & 3KO-H-island169L in Table 3). In three separate experiments, (on average) 10-fold higher Kan[R] transformants were found when kan was reading leftward from the position of O-island #169 (according to the numbering in the sequence file) instead of rightward. This leftward reading direction of the kan gene places it colinear with other genes in this region (ytfB and Z5814) and supports the notion that proper positioning of the drug marker in the chromosome can influence the recovery of the recombinant.

This context effect was also seen with one of the long homology substrates at the eae locus. Initial attempts to generate the EHEC chromosomal replacement using the fragment from pKM184 (containing eae::cat) yielded no recombinants with repeated attempts. The orientation of the cat gene inserted within the eae flanking regions of pKM184 was determined, and found to be reading opposite to the direction of the endogenous eae gene. Thus, a version of pKM184 was constructed where the cat gene was inserted co-directionally with eae. Electroporation with this substrate readily yielded recombinants (see Table 4, lines 1, 4-5).

Thus, the orientation of the drug marker within the target gene site can effect either its expression level (affecting the selection of the recombinant) or its ability to be stably incorporated into the chromosome. With difficult substitutions, both orientations of the drug marker (or the use of properly positioned transcription terminators within the plasmid construct) should be attempted. Context dependent marker expression may be one of the primary causes of the variation seen among Red-promoted gene replacements of the same drug marker placed at different loci along the E. coli K-12 and Salmonella enterica Serovar typhimurium chromosomes.

Example 6

Extended Expression of Red and Gam is Mutagenic

Unlike E. coli K-12 and Salmonella enterica Serovar Typhimurium, there are no phage transductional protocols for EHEC to place λ Red-generated deletion alleles into clean genetic backgrounds. Thus, it was important to consider the possible mutagenic profile of λ Red expression in EHEC. Somewhat surprisingly, overnight cultures of EHEC containing uncontrolled expression of red and gam from pKM201 (which does not express lacI) showed a 10-fold increase in the rate of spontaneous rifampicin resistance (FIG. 4). EHEC containing pKM208 (which expresses the lacI repressor as well as the Ptac-red-gam operon) showed a significant increase in rifampicin resistance only when incubated in the presence of IPTG overnight.

In order to determine the minimum time of Red induction required to generate the hyper-rec phenotype, the frequency of gene replacement was measured as a function of IPTG induction. FIG. 5 shows that a 20 minute exposure to IPTG is sufficient to induce the hyper-rec phenotype in EHEC. For most of the experiments reported above, a 1 hour IPTG induction period was used. Thus, EHEC cells were examined to determine whether Red induction for 1 hour induced a mutagenic phenotype. EHEC cells containing pKM208 were exposed to IPTG for 1 hour in a manner identical that used for the preparation of electrocompetent cells, and plated on LB plates containing rifampicin. No increase in Rif[R] cells were seen in such preparations when compared to uninduced cultures (see FIG. 5, insert). The same was result was seen with EHEC containing pTP223 (data not shown). Thus, while uncontrolled expression of Red and Gam causes a 10-fold increase in mutagenesis, limited expression of Red and Gam required for establishment of the hyper-rec phenotype is not mutagenic.

Example 7

λ Red-promoted PCR-Mediated Recombination in EPEC

Red and Gam-producing plasmid pKD46 has been reported for use in long homology recombination of plasmids with the EPEC chromosome, but not short homology PCR-mediated recombination. Thus, certain of the above-described plasmids were tested in EPEC for Red-promoted PCR-mediated recombination. It was not possible to transform EPEC with either of the pSC101-origin containing plasmids pKM201 or pKM208. However, it was possible to electroporate EPEC with pTP223. Surprisingly, and unlike the case with EHEC, pTP223 did promote efficient short homology recombination with PCR substrates.

This plasmid has been used to construct an EPECΔtir construct (Campellone et al., 2002). A 13 kb deletion has also been constructed within the locus of enterocyte effacement in EPEC (KC21) in a manner similar to that described above for EHEC (described in Table 1), with the exception that pTP223 was used to supply λ Red and Gam. Also, it has been observed that the heat shock step plays a stimulatory role in Red-promoted PCR-mediated EPEC gene replacement. In one set of experiments, the heat shock step with EPEC resulted in 2-10 fold increase in the number of recombinants (corresponding to a 20-100 fold increase in frequency of recombinants per survivor of electroporation). The effect of the heat shock step is quite variable, however, as the stimulation of recombinants per survivor using the Δlac::kan allele in EHEC to was found to be only 2-4 fold.

Discussion of Examples 1-7

The ability to inactivate or replace a gene of interest in the chromosomes of bacterial pathogens is a critical step in the identification of virulence factors, and in the elucidation of mechanisms of infectivity. However, gene replacement protocols for most pathogenic bacteria prove difficult and time consuming. The above Examples demonstrate that λ Red can be utilized for the manipulation of the chromosomes of EHEC and EPEC. The value of such a system has been demonstrated by observing a difference in phenotype for bacteria expressing an engineered virulence factor from a plasmid versus its normal chromosomal location.

Two schemes have been presented for engineering the chromosomes of EHEC and EPEC. In one case, plasmids are constructed that contain a drug marker flanked by upstream and downstream regions of the target gene. The plasmid is digested with the appropriate restriction enzymes, liberating the recombinant fragment (substrate) which is electroporated into Red-producing cells. The frequency of simple plasmid transformants can be decreased by digesting the plasmid with backbone-specific restriction enzymes prior to electroporation. As an alternative, the marked deletions can be constructed in plasmids with conditional replicons, such as those that require the trans-acting π protein (the pir gene product) for replication (Metcalf et al., 1996), though such plasmids were not used in this study. Electroporation of a linear DNA containing the marked deletion generates a gene replacement without the need for plasmid co-integrant formation and resolution.

In the case where a counter-selectable marker is placed on the EHEC or EPEC chromosome (e.g., sacB), the target gene can be replaced with any site-directed mutant generated in vitro simply by electroporation of a linear fragment containing the mutated allele. While this scheme requires prior construction of the deleted or modified allele on a plasmid, it is useful in situations where multiple mutant alleles need to be crossed on to the chromosome, as was presented here with the hybrid tir constructs. In addition, precise in-frame deletions can be easily constructed (see Table 5). The benefits of generating precise deletions for genetic analysis are clear relative to transposon mutagenesis procedures, where one cannot be if sure the entire gene is inactivated, or whether an insertion affects downstream functions within an operon (i.e., polarity effects). Finally, the Red-producing plasmids described here, (including pTP223 which does not have a temperature sensitive origin of replication) are unstable following induction with IPTG (10-50% of the transformants lose the plasmid). This is surprising benefit, as gene replacement and plasmid curing occurs simultaneously after electroporation, and such transformants can be found by screening. Transformants cured of the plasmid and modified at the gene of interest are readily available for in vitro and in vivo analyses.

The expression of native and mutant genes from low copy number plasmids (in the context of a chromosomal deletion of the gene) has been a common method to assess the function of virulence factors in bacterial pathogens. One must be careful to note, however, that expression from low copy number plasmids does not always reflect the phenotype of native (chromosomal) expression patterns of these genes. The expression of hybrid Tir molecules reported here is a prime example. Despite the similarities between chromosome and plasmid-encoded expression of these modified genes, the Tir-HHH$_{NBS}$ hybrid protein exhibited its mutant phenotype (extended pedestals) only when it was expressed from the chromosome.

It is currently unknown whether the differences within this Tir hybrid that create the long pedestal phenotype are directly related to the interaction of the cytoplasmic domains with host cell components, due to changes in Tir structure in the context of the chimera, or from altering the association of other substrates with the type III apparatus. Clearly, the masking of the long pedestal phenotype associated with overexpression of Tir-HHH$_{NBS}$ from a plasmid-encoding locus highlights the importance of directing the expression of bacterial products from their endogenous loci. The ability to engineer the chromosomes of pathogenic *E. coli* with lambda Red recombination greatly facilitates such genetic analyses.

In the second scheme for EHEC or EPEC gene replacement, one-step gene or pathogenicity island deletion is performed by electroporation of PCR fragments containing a drug marker flanked by 40 bp of target DNA. The ease of this system makes it preferable when multiple target genes must be precisely deleted for genetic or in vivo analysis. The versatility of the system is highlighted by the range of chromosomal segments that λ Red can act on, deleting pathogenicity islands as small as 733 bp and as large as 45 kb. However, in performing short homology recombination in EHEC, a reduction in efficiency relative to that seen in *E. coli* K-12 was noticed. One possibility to explain these results is that the λ Gam protein might not be as active on EHEC RecBCD as it is for *E. coli* K-12 RecBCD. This seemed unlikely given the conservation of the recBCD genes between these two species (97-98% conservation). Nonetheless, a EHEC ΔrecC::cat knockout was made and tested its ability to perform Red-mediated SHR. Deactivating RecBCD function by deletion of recC did not stimulate λ Red recombination in EHEC at the lacZ locus (data not shown). Thus, to a first approximation, λ Gam works as efficiently with EHEC RecBCD as it does with *E. coli* K-12 RecBCD. Another possibility is that the red functions from the endogenous lambdoid EHEC prophage 933W would be better suited than wild type λ red for gene replacement in EHEC. This seems unlikely given the high degree of conservation between λ and 933W red genes (99.6% identity), and was not tested.

Despite this lower frequency of Red recombination in EHEC (as judged by recombination in the lacZ locus), λ Red works at an efficiency that appears to allow any non-essential regions of the chromosome to be manipulated. This is true for EPEC as well when red and gam are expressed from plasmid pTP223. It is curious that pTP223 works well in EPEC, but not in EHEC or *E. coli* K-12 for PCR-mediated Red recombination. Perhaps in EPEC, pTP223 does not replicate by extensive rolling-circle replication as was seen for *E. coli* K-12, thus preventing linear multimers of the plasmid from interfering with Red function. This hypothesis, however, has not been tested.

Another interesting observation reported here is the mutagenic phenotype of constitutive red overexpression. Perhaps the annealing function of Bet interferes with mismatch repair pathway of *E. coli* by reannealing the unwound ssDNA generated by UvrD, thus interfering with the progression of the mismatch repair process (see Hsieh (2001) for review). Even though Red can substitute for RecBCD in recombinational repair and conjugation (Murphy, 1998), the mutagenesis associated with Red may explain why many bacterial species do not possess a constitutive phage-like recombination system as their primary recombination pathway, and instead employ the more rigorous Chi-activated RecBCD dsDNA exonuclease to generate recombinant intermediates (a pathway that does not involve a known Bet-like ssDNA annealing protein).

The mutagenic phenotype of constitutive Red expression (and possibly RecET as well) highlights the importance of controlling these functions in vivo when using them for gene replacement in pathogenic bacteria (i.e., limiting their expression to a recombinogenic window). EHEC and EPEC containing Red and Gam-producing plasmids may also be amenable to ssDNA oligo-directed chromosomal alterations and in vivo cloning by gap repair, as has been demonstrated with *E. coli* K-12 strains expressing phage recombination functions (Ellis et al., 2001; Lee et al., 2001; Zhang et al., 2000). The λ Red recombination system can be adapted for use in *Pseudomonas aeruginosa*, and other bacterial pathogens. Manipulation of the chromosomes of other pathogenic organisms allows analysis of a variety of bacterial pathogenic mechanisms. Moreover, the genomes of several clinically relevant bacteria have been sequenced, and thousands of new genes are now available for genetic analysis.

REFERENCES

Baudin, A., Ozier-Kalogeropoulos, O., Denouel, A., Lacroute, F. and Cullen, C. (1993) A simple and efficient method for direct gene deletion in *Saccharomyces cerevisiae*. *Nucleic Acid Res.* 21: 3329-3330.

Campellone, K. G., Giese, A., Tipper, D. J. and Leong, J. M. (2002) A tyrosine-phosphorylated 12-amino-acid sequence of enteropathogenic *Escherichia coli* Tir binds the host adaptor protein Nck and is required for Nck localization to actin pedestals. *Mol Microbiol* 43: 1227-1241.

Chakravortty, D., Hansen-Wester, I. and Hensel, M. (2002) *Salmonella* pathogenicity island 2 mediates protection of intracellular *Salmonella* from reactive nitrogen intermediates. *J Exp Med* 195: 1155-1166.

Clegg, S. and Hughes, K. T. (2002) FimZ Is a Molecular Link between Sticking and Swimming in *Salmonella enterica* Serovar Typhimurium 1213. *J Bacteriol* 184: 1209-1213.

Court, D. L., Sawitzke, J. A. and Thomason, L. C. (2002) Genetic engineering using homologous recombination. *Annu Rev Genet* 36: 361-388.

Datsenko, K. A. and Wanner, B. L. (2000) One-step inactivation of chromosomal genes in *Escherichia coli* K-12 using PCR products. Proc Natl Acad Sci USA 97: 6640-6645.

Day, W. A., Reinaldo, E. F. and Maurelli, A. T. (2001) Pathoadaptive mutations that enhance virulence: genetic organization of the cadA regions of *Shigella* ssp. *Infect Immun* 69: 7471-7480.

de Grado, M., Abe, A., Gauthier, A., Steele-Mortimer, O., DeVinney, R., and Finlay, B.B. (1999) Identification of the intimin-binding domain of Tir of enteropathogenic *Escherichia coli*. *Cell Microbiol* 1: 7-17.

Deibel, C., Kramer, S., Chakraborty, T., and Ebel, F. (1998) EspE, a novel secreted protein of attaching and effacing bacteria, is directly translocated into infected host cells, where it appears as a tyrosine-phosphorylated 90 kDa protein. *Mol Microbiol* 28: 463-474.

DeVinney, R., Stein, M., Reinscheid, D., Abe, A., Ruschkowski, S. and Finlay, B. B. (1999) Enterohemorrhagic *Escherichia coli* O157:H7 produces Tir, which is translocated to the host cell membrane but is not tyrosine phosphorylated. *Infect Immun* 67: 2389-2398.

Donnenberg, M. S., and Kaper, J. B. (1991) Construction of an eae deletion mutant of enteropathogenic *Escherichia coli* by using a positive-selection suicide vector. *Infect Immun*, 59: 4310-4317.

Donnenberg, M. S., Tzipori, S., McKee, M. L., O'Brien, A. D., Alroy, J. and Kaper, J. B. (1993) The role of the eae gene of enterohemorrhagic *Escherichia coli* in intimate attachment in vitro and in a porcine model. *J Clin Invest* 92: 1418-1424.

Ellis, H. M., Yu, D., DiTizio, T. and Court, D. L. (2001) High efficiency mutagenesis, repair, and engineering of chromosomal DNA using single-stranded oligonucleotides. *Proc Natl Acad Sci USA* 98(12): 6742-6746.

Farinha, M. A., and Kropinski, A. M. (1990) High efficiency electroporation of *Pseudomonas aeruginosa* using frozen cell suspensions. *FEMS Microbiol Lett*, 70: 221-226.

Frankel, G., Phillips, A. D., Rosenshire, I., Dougan, G., Kaper, J., and Knutton, S. (1998) Enteropathogenic and enterohaemorrhagic *Escherichia coli*; more submersive elements. 30: 911-921.

Freeman, J. A., Rappl, C. V., Kuhle, V., Hensel, M. and Miller, S. I. (2002) SpiC Is Required for Translocation of *Salmonella* Pathogenicity Island 2 Effectors and Secretion of Translocon Proteins SseB and SseC. *J Bacteriol* 184: 4971-4980.

Hamilton, C. M., Aldea, M., Washburn, B. K., Babitzke, P. and Kushner, S. R. (1989) New method for generating deletions and gene replacements in *Escherichia coli*. *J Bacteriol* 171: 4617-4622.

Hartland, E. L., Batchelor, M., Delahay, R. M., Hale, C., Matthews, S., Dougan, G., et al. (1999) Binding of intimin from enteropathogenic *Escherichia coli* to Tir and to host cells. *Mol Microbiol* 32: 151-158.

Havemann, G. D., Sampson, E. M. and Bobik, T. A. (2002) PduA Is a Shell Protein of Polyhedral Organelles Involved in Coenzyme B12-Dependent Degradation of 1,2-Propanediol in *Salmonella enterica* Serovar Typhimurium LT2. *J Bacteriol* 184: 1253-1261.

Hsieh P., (2001) Molecular mechanisms of DNA mismatch repair. *Mutat Res* 486:71-87

Jerse, A. E., Yu, J., Tall, B. D., and Kaper, J. B. (1990) A genetic locus of enteropathogenic *Escherichia coli* necessary for the production of attaching and effacing lesions on tissue culture cells. *Proc Natl Acad Sci USA,* 87: 7839-7843.

Kenny, B., DeVinney, R., Stein, M., Reinscheid, D. J., Frey, E. A. and Finlay, B. B. (1997) Enteropathogenic *E. coli* (EPEC) transfers its receptor for intimate adherence into mammalian cells. Cell 91: 511-520.

Kenny, B. (1999) Phosphorylation of tyrosine 474 of the enteropathogenic *Escherichia coli* (EPEC) Tir receptor molecule is essential for actin nucleating activity and is preceded by additional host modifications. *Mol Microbiol* 31: 1229-1241.

Kenny, B. (2001) The enterohaemorrhagic *Escherichia coli* (serotype O157:H7) Tir molecule is not functionally interchangeable for its enteropathogenic *E. coli* (serotype O127:H6) homologue. *Cell Microbiol* 3: 499-510.

Lee, E. C., Yu, D., Martinez de Velasco, J., Tessarollo, L., Swing, D. A., Court, D. L., Jenkins, N. A. and Copeland, N. G. (2001) A highly efficient *Escherichia coli*-based chromosome engineering system adapted for recombinogenic targeting and subcloning of BAC DNA. *Genomics* 73: 56-65.

Liu, H., Magoun, L., Luperchio, S., Schauer, D. B., and Leong, J. M. (1999) The Tir-binding region of enterohaemorrhagic *Escherichia coli* intimin is sufficient to trigger actin condensation after bacterial-induced host cell signalling. Mol Microbiol 34: 67-81.

Liu, H., and Radhakrishnan, P., and Magoun, L., and Prabu, M., and Campellone, K. G., and Savage, P., et al. (2002) Point mutants of EHEC intimin that diminish Tir recognition and actin pedestal formation highlight a putative Tir binding pocket. *Mol Microbiol,* 45: 1557.

Lorenz, M. C., Muir, R. S., Lim, E., McElver, J., Weber, S. C. and Heitman, J. (1995) Gene disruption with PCR products in *Saccharomyces cerevisiae. Gene* 158: 113-117.

Lu, S., Killoran, P. B., Fang, F. C. and Riley, L. W. (2002) The Global Regulator ArcA Controls Resistance to Reactive Nitrogen and Oxygen Intermediates in *Salmonella enterica* Serovar Enteritidis. *Infect Immun* 70: 451-461.

McDaniel, T. K., and Kaper, J. B. (1997) A cloned pathogenicity island from enteropathogenic *Escherichia coli* confers the attaching and effacing phenotype on *E. coli* K-12. *Mol Microbiol* 23: 399-407.

McKee, M. L., Melton-Celsa, A. R., Moxley, R. A., Francis, D. H. and O'Brien, A. D. (1995) Enterohemorrhagic *Escherichia coli* O157:H7 requires intimin to colonize the gnotobiotic pig intestine and to adhere to HEp-2 cells. *Infect Immun* 63: 3739-3744.

Metcalf, W., Jiang, W., Daniels, L., Kim, S., Haldimann, A. and Wanner, B. (1996) Conditionally replicative and conjugative plasmids carrying lacZ alpha for cloning, mutagenesis, and allele replacement in bacteria. *Plasmid* 35: 1-13.

Murphy, K. C. (1998) Use of bacteriophage λ recombination functions to promote gene replacement in *Escherichia coli. J Bacteriol* 180: 2063-2071.

Murphy, K. C., Campellone, K. G. and Poteete, A. R. (2000) PCR-mediated gene replacement in *Escherchia coli. Gene* 246: 321-330.

Nataro, J. P. and Kaper, J. B. (1998) Diarrheagenic *Escherichia coli. Clin Microbiol Rev* 11: 142-201.

Perna, N. T., Mayhew, G. F., Posfai, G., Elliott, S., Donnenberg, M. S., Kaper, J. B., and Blattner, F. R. (1998) Molecular evolution of a pathogenicity island from enterohemorrhagic *Escherichia coli* O157:H7. *Infect Immun* 66: 3810-3817.

Perna, N. T., Plunkett, G., Burland, V., Mau, B., Glasner, J. D., Rose, D. J., Mayhew, G. F., Evans, P. S., Gregor, J., Kirkpatrick, H. A., Posfai, G., Hackett, J., Klink, S., Boutin, A., Shao, Y., Miller, L., Grotbeck, E. J., Davis, N. W., Lim, A., Dimalanta, E. T., Potamousis, K. D., Apodaca, J., Anantharaman, T. S., Lin, J., Yen, G., Schwartz, D. C., Welch, R. A. and Blattner, F. R. (2001) Genome sequence of enterohaemorrhagic *Escherichia coli* O157:H7. *Nature* 409: 529-533.

Poteete, A. R. and Fenton, A. C. (1984) Lambda red-dependent growth and recombination of phage P22. *Virology* 134: 161-167.

Poteete, A. R., Fenton, A. C. and Murphy, K. C. (1988) Modulation of *Escherichia coli* RecBCD activity by the bacteriophage λ Gam and P22 Abc functions. *J Bacteriol* 170: 2012-2021.

Poteete, A. R., Fenton, A. C. and Murphy, K. C. (1999) Roles of RuvC and RecG in phage λ Red-mediated recombination. *J Bacteriol* 181: 5402-5408.

Price-Carter, M., Tingey, J., Bobik, T. A. and Roth, J. R. (2001) The Alternative Electron Acceptor Tetrathionate Supports B12-Dependent Anaerobic Growth of *Salmonella enterica* Serovar Typhimurium on Ethanolamine or 1,2-Propanediol. *J Bacteriol* 183: 2463-2475.

Rosenshine, I., Ruschkowski, S., Stein, M., Reinscheid, D. J., Mills, S. D., and Finlay, B. B. (1996) A pathogenic bacterium triggers epithelial signals to form a functional bacterial receptor that mediates actin pseudopod formation. *EMBO J* 15: 2613-2624.

Semerjian, A. V., Malloy, D. C., and Poteete, A. R. (1989) Genetic structure of the bacteriophage P22 $P_L$ Operon. *J Mol Biol* 207: 1-13.

Stanley, T. L., Ellermeier, C. D. and Slauch, J. M. (2000) Tissue-Specific Gene Expression Identifies a Gene in the Lysogenic Phage Gifsy-1 That Affects *Salmonella enterica* Serovar Typhimurium Survival in Peyer's Patches. *J Bacteriol* 186: 4406-4413.

Tzipori, S., Gunzer, F., Donnenberg, M. S., de Montigny, L., Kaper, J. B., and Donohue-Rolfe, A. (1995) The role of the eaeA gene in diarrhea and neurological complications in a gnotobiotic piglet model of enterohemorrhagic *Escherichia coli* infection. *Infect Immun* 63: 3621-3627.

Umanski, T., Rosenshine, I. and Friedberg, D. (2002) Thermoregulated expression of virulence genes in enteropathogenic *Escherichia coli. Microbiology* 148: 2735-2744.

Uzzau, S., Figueroa-Bossi, N., Rubino, S. and Bossi, L. (2001) Epitope tagging of chromosomal genes in *Salmonella. Proc Natl Acad Sci USA* 98: 15264-15269.

Vallance, B. A., Chan, C., Robertson, M. L., and Finlay, B. B. (2002) Enteropathogenic and enterohemorrhagic *Escherichia coli* infections: Emerging themes in pathogenesis and prevention. *Can J Gastroenterol,* 16: 771-778.

Wach, A., Brachat, A., Pohlmann, R. and Philippsen, P. (1994) New heterologous modules for classical or PCR-based gene disruptions in *Saccharomyces cerevisiae. Yeast* 10: 1793-1808.

Wilson, R. K., Shaw, R. K., Daniell, S., Knutton, S. and Frankel, G. (2001) Role of EscF, a putative needle complex protein, in the type III protein translocation system of enteropathogenic *Escherichia coli. Cell Microbiol* 3: 753-762.

Worlock, A. J. and Smith, R. L. (2002) ZntB Is a Novel Zn2+ Transporter in *Salmonella enterica* Serovar Typhimurium. *J Bacteriol* 184: 4369-4373.

Yu, D., Ellis, H. M., Lee, E. C., Jenkins, N. A., Copeland, N. G. and Court, D. L. (2000) An efficient recombination system for chromosome engineering in *Escherichia coli*. *Proc Natl Acad Sci USA* 97(11): 5978-5983.

Yu, J. and Kaper, J. B. (1992) Cloning and characterization of the eae gene of enterhaemorrhagic *Escherichia coli* O157: H7. *Mol Microbiol* 6: 411-417

Zhang, Y., Buchholz, F., Muyrers, J. P. and Stewart, A. F. (1998) A new logic for DNA engineering using recombination in *Escherichia coli*. *Nat Genet* 20: 123-128.

Zhang, Y., Muyrers, J. P., Testa, G. and Stewart, A. F. (2000) DNA cloning by homologous recombination in *Escherichia coli*. *Nat Biotechnol* 18: 1314-1317.

Equivalents Those skilled in the art will recognize, or be able to ascertain using no more than routine experimentation, many equivalents to the specific embodiments of the invention described herein. Such equivalents are intended to be encompassed by the following claims.

What is claimed:

1. A recombinant organism comprising a recombinant vector comprising:
   (a) a λ exo and a λ bet nucleotide sequences encoding bacteriophage λ Red recombinase;
   (b) a λ gam nucleotide sequence encoding bacteriophage anti-RecBCD;
   (c) a Ptac promoter sequence operably linked to the nucleotide sequence of (a) and (b); and
   (d) a nucleotide sequence encoding LacI operably linked to its native promoter; and
   (e) at least one origin of replication sequence which confers low copy number on the vector,
   wherein the recombinant organism is a bacterial species which is pathogenic to humans, animals, or plants, and whereby the products of the recombinant vector facilitate replacement of genomic nucleic acid in the recombinant organism with substrate nucleic acid.

2. The pathogenic species of claim 1 which is a strain of *Escherichia coli* which is pathogenic to humans, animals, or plants.

3. The pathogenic species of claim 2 which is enterohemorrhagic *E. coli* (EHEC) or enteropathogenic *E. coli* (EPEC).

4. The pathogenic species of claim 1 which is of the genus *Pseudomonas*.

5. The pathogenic species of claim 4, which is *Pseudomonas aeruginosa*.

6. The pathogenic species of claim 1 which is of the genus *Mycobacterium*.

7. The pathogenic species of claim 6, which is *Mycobacterium tuberculosis*.

8. The vector of claim 1, wherein the at least one origin of replication sequence is temperature sensitive.

9. A recombinant organism comprising a recombinant vector comprising:
  (a) a λ exo and a λ bet nucleotide sequences encoding bacteriophage λ Red recombinase;
  (b) a λ gam nucleotide sequence encoding bacteriophage anti-RecBCD;
  (c) a Ptac promoter sequence operably linked to the nucleotide sequence of (a) and (b); and
  (d) a nucleotide sequence encoding LacI operably linked to its native promoter; and
  (e) at least one origin of replication sequence which confers low copy number on the vector,
wherein the recombinant organism is enterohemorrhagic *E. coli* (EHEC) or enteropathogenic *E. coli* (EPEC), and whereby the products of the recombinant vector facilitate replacement of genomic nucleic acid in the recombinant organism with substrate nucleic acid.

10. A recombinant organism comprising a recombinant vector comprising:

(a) a λ exo and a λ bet nucleotide sequences encoding bacteriophage λ Red recombinase;

(b) a λ gain nucleotide sequence encoding bacteriophage anti-RecBCD;

(c) a Ptac promoter sequence operably linked to the nucleotide sequence of (a) and (b); and (d) a nucleotide sequence encoding LacI operably linked to its native promoter; and (e) at least one origin of replication sequence which confers low copy number on the vector, wherein the recombinant organism is *Pseudomonas aeruginosa*, and whereby the products of the recombinant vector facilitate replacement of genomic nucleic acid in the recombinant organism with substrate nucleic acid.

11. A recombinant organism comprising a recombinant vector comprising:

(a) a λ exo and a λ bet nucleotide sequences encoding bacteriophage λ Red recombinase;

(b) a λ gam nucleotide sequence encoding bacteriophage anti-RecBCD;

(c) a Ptac promoter sequence operably linked to the nucleotide sequence of (a) and (b); and (d) a nucleotide sequence encoding LacI operably linked to its native promoter; and (e) at least one origin of replication sequence which confers low copy number on the vector, wherein the recombinant organism is *Mycobacteriuin tuberculosis*, and whereby the products of the recombinant vector facilitate replacement of genomic nucleic acid in the recombinant organism with substrate nucleic acid.

* * * * *

UNITED STATES PATENT AND TRADEMARK OFFICE
CERTIFICATE OF CORRECTION

| | | |
|---|---|---|
| PATENT NO. | : 7,468,269 B2 | Page 1 of 1 |
| APPLICATION NO. | : 10/789186 | |
| DATED | : December 23, 2008 | |
| INVENTOR(S) | : Kenan C. Murphy | |

It is certified that error appears in the above-identified patent and that said Letters Patent is hereby corrected as shown below:

At column 1, line 15 to line 18, of the printed patent:

"This invention was made at least in part with government support under grant no. R21-GM62482 awarded by the National Institutes of Health. The government may have certain rights in this invention."

should be

--This invention was made with government support under Grant no. GM062482 awarded by the National Institutes of Health. The government has certain rights in the invention.--

Signed and Sealed this

Twenty-eighth Day of April, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,468,269 B2 | Page 1 of 1 |
| APPLICATION NO. | : 10/789186 | |
| DATED | : December 23, 2008 | |
| INVENTOR(S) | : Murphy | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 258 days.

Delete the phrase "by 258 days" and insert -- by 329 days --

Signed and Sealed this

Twenty-second Day of June, 2010

David J. Kappos
*Director of the United States Patent and Trademark Office*

```
                            SEQUENCE LISTING

<160> NUMBER OF SEQ ID NOS: 37

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
atcatcgagc tcaccgagca gttctcgatt gctatt                              36

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
ttagacgaat gcggccgcaa taggcataaa tatctccttt tt                       42

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
atgcctattg cggccgcatt cgtctaaata tatccataat ca                       42

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
atcatcgcat gccaccagaa aaatcctgat caatga                              36

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
atcatcgagc tcggaaatgc gattccgtca                                     30

<210> SEQ ID NO 6
<211> LENGTH: 42
```

```
<212> TYPE: DNA
<213> ORGANISM: Artificial Sequence
<220> FEATURE:
<223> OTHER INFORMATION: Primer

<400> SEQUENCE: 6
ttattctact gcggccgcag taatcatgtt atggctccac ca                42

<210> SEQ ID NO 7
<211> LENGTH: 42
<212> TYPE: DNA
<213> ORGANISM: Artificial Sequence
<220> FEATURE:
<223> OTHER INFORMATION: Primer

<400> SEQUENCE: 7
atgattactg cggccgcagt agaataattc cataaccacc cc                42

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
atcatcgcat gctaaaactt ctcaatggtg cgatgc                       36

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
atcatcggta ccgcacgtca gtttgctctt caagag                       36

<210> SEQ ID NO 10
<211> LENGTH: 50
<212> TYPE: DNA
<213> ORGANISM: Artificial Sequence
<220> FEATURE:
<223> OTHER INFORMATION: Primer

<400> SEQUENCE: 10
tgccgatcaa cgtctcatgc ggccgcaggt aatggaggtg caggaggaat        50

<210> SEQ ID NO 11
<211> LENGTH: 50
<212> TYPE: DNA
<213> ORGANISM: Artificial Sequence
<220> FEATURE:
<223> OTHER INFORMATION: Primer

<400> SEQUENCE: 11
aatggcagaa attcgaaagc ggccgcgaat acttcgaata acccaccagc        50

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
```

```
tcatcaggta cctcggtcat gttgcttttg gtcacg                                    36

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13
gacgggttgt tactcgctca catttaatgt tgatgaaagc gcggccgcat gagacgttga         60

<210> SEQ ID NO 14
<211> LENGTH: 60
<212> TYPE: DNA
<213> ORGANISM: Artificial Sequence
<220> FEATURE:
<223> OTHER INFORMATION: Primer

<400> SEQUENCE: 14
aagaaagcct gactggcggt taaattgcca acgcttatta gcggccgctt tcgaatttct         60

<210> SEQ ID NO 15
<211> LENGTH: 72
<212> TYPE: DNA
<213> ORGANISM: Artificial Sequence
<220> FEATURE:
<223> OTHER INFORMATION: Primer

<400> SEQUENCE: 15
atgcttaatg gaattagtaa cgctgcttct acactagggc ggcagcttgt agcggccgca         60
tgagacgttg at                                                             72

<210> SEQ ID NO 16
<211> LENGTH: 73
<212> TYPE: DNA
<213> ORGANISM: Artificial Sequence
<220> FEATURE:
<223> OTHER INFORMATION: Primer

<400> SEQUENCE: 16 ttacccttc ttcgattgct cataggcagc taaatgatct tttaatgcct ggcggccgct          60
ttcgaatttc tgc                                                            73

<210> SEQ ID NO 17
<211> LENGTH: 81
<212> TYPE: DNA
<213> ORGANISM: Artificial Sequence
<220> FEATURE:
<223> OTHER INFORMATION: Primer

<400> SEQUENCE: 17
atgcctattg gtaatcttgg tcataatccc aatgtgaata attcaattcc tcctgcacct         60
cgcggccgca tgagacgttg a                                                   81

<210> SEQ ID NO 18
<211> LENGTH: 79
<212> TYPE: DNA
<213> ORGANISM: Artificial Sequence
<220> FEATURE:
<223> OTHER INFORMATION: Primer

<400> SEQUENCE: 18
gatatattta gacgaaacga tgggatcccg gcgctggtgg gttattcgaa gtattcacag         60
```
cggccgcttt cgaatttct                                           79

<210> SEQ ID NO 19
<211> LENGTH: 75
<212> TYPE: DNA
<213> ORGANISM: Artificial Sequence
<220> FEATURE:
<223> OTHER INFORMATION: Primer

<400> SEQUENCE: 19
tttctgttat cattactgcc aatatttgtt gttattggta cttcattcct gaaagcggcc    60
gcatgagacg ttgat                                               75

<210> SEQ ID NO 20
<211> LENGTH: 76
<212> TYPE: DNA
<213> ORGANISM: Artificial Sequence
<220> FEATURE:
<223> OTHER INFORMATION: Primer

<400> SEQUENCE: 20
aaagctgtcg aaatattaat cgcgataatg atatccacca caactgttgg tagtgcggcc    60
gctttcgaat ttctgc                                              76

<210> SEQ ID NO 21
<211> LENGTH: 70
<212> TYPE: DNA
<213> ORGANISM: Artificial Sequence
<220> FEATURE:
<223> OTHER INFORMATION: Primer

<400> SEQUENCE: 21
aagtatttta ttgaattcat ttaaagataa ttatcttagc attattcagg cggccgcatg    60
agacgttgat                                                     70

<210> SEQ ID NO 22
<211> LENGTH: 72
<212> TYPE: DNA
<213> ORGANISM: Artificial Sequence
<220> FEATURE:
<223> OTHER INFORMATION: Primer

<400> SEQUENCE: 22
tgttcttctg atatccagaa acgcccctca tagcccgagt atgtcaacgt gcggccgctt    60
tcgaatttct gc                                                  72

<210> SEQ ID NO 23
<211> LENGTH: 60
<212> TYPE: DNA
<213> ORGANISM: Artificial Sequence
<220> FEATURE:
<223> OTHER INFORMATION: Primer

<400> SEQUENCE: 23
ctgacactga gcgccgggca taagcagggc aagagcggtg aatctctgat gttacattgc    60

<210> SEQ ID NO 24
<211> LENGTH: 60
<212> TYPE: DNA
<213> ORGANISM: Artificial Sequence
<220> FEATURE:
<223> OTHER INFORMATION: Primer

```
<400> SEQUENCE: 24
cctctttccg ctatgaaggt gagtgggagc actaccctga ttcaactcag caaaagttcg      60

<210> SEQ ID NO 25
<211> LENGTH: 60
<212> TYPE: DNA
<213> ORGANISM: Artificial Sequence
<220> FEATURE:
<223> OTHER INFORMATION: Primer

<400> SEQUENCE: 25
agccaggtca acaggtcagt atgggaaggc gaacaactcg aatctctgat gttacattgc      60

<210> SEQ ID NO 26
<211> LENGTH: 60
<212> TYPE: DNA
<213> ORGANISM: Artificial Sequence
<220> FEATURE:
<223> OTHER INFORMATION: Primer

<400> SEQUENCE: 26
tgttgttaat gacatccgat ctcaccgcgt ggggcatgga ttcaactcag caaaagttcg      60

<210> SEQ ID NO 27
<211> LENGTH: 60
<212> TYPE: DNA
<213> ORGANISM: Artificial Sequence
<220> FEATURE:
<223> OTHER INFORMATION: Primer

<400> SEQUENCE: 27
ttgacatcct ccacgccctg aatgacgagg atccctgcta aatctctgat gttacattgc      60

<210> SEQ ID NO 28
<211> LENGTH: 60
<212> TYPE: DNA
<213> ORGANISM: Artificial Sequence
<220> FEATURE:
<223> OTHER INFORMATION: Primer

<400> SEQUENCE: 28
ggtgcgccgt aaaacccgt ccttcagggc ggggatataa ttcaactcag caaaagttcg       60

<210> SEQ ID NO 29
<211> LENGTH: 60
<212> TYPE: DNA
<213> ORGANISM: Artificial Sequence
<220> FEATURE:
<223> OTHER INFORMATION: Primer

<400> SEQUENCE: 29
gcaaatctga gcctgacgca agcatcgggc agaaattaat aatctctgat gttacattgc      60

<210> SEQ ID NO 30
<211> LENGTH: 60
<212> TYPE: DNA
<213> ORGANISM: Artificial Sequence
<220> FEATURE:
<223> OTHER INFORMATION: Primer

<400> SEQUENCE: 30
tgcccgtaat ttgagctcga aatatttagt cgtaattttg ttcaactcag caaaagttcg      60

<210> SEQ ID NO 31
<211> LENGTH: 60
```

<210> SEQ ID NO 31
<211> LENGTH: 60
<212> TYPE: DNA
<213> ORGANISM: Artificial Sequence
<220> FEATURE:
<223> OTHER INFORMATION: Primer

<400> SEQUENCE: 31
ccggtgcgcc gtaaaacccc gtccttcagg cggggatat aatctctgat gttacattgc    60

<210> SEQ ID NO 32
<211> LENGTH: 60
<212> TYPE: DNA
<213> ORGANISM: Artificial Sequence
<220> FEATURE:
<223> OTHER INFORMATION: Primer

<400> SEQUENCE: 32
ttgacatcct ccaagccctg aaggacgtgg atccctgcta ttcaactcag caaaagttcg    60

<210> SEQ ID NO 33
<211> LENGTH: 60
<212> TYPE: DNA
<213> ORGANISM: Artificial Sequence
<220> FEATURE:
<223> OTHER INFORMATION: Primer

<400> SEQUENCE: 33
ccggtgcgcc gtaaaacccc gtccttcagg cggggatat ttcaactcag caaaagttcg    60

<210> SEQ ID NO 34
<211> LENGTH: 60
<212> TYPE: DNA
<213> ORGANISM: Artificial Sequence
<220> FEATURE:
<223> OTHER INFORMATION: Primer

<400> SEQUENCE: 34
ttgacatcct ccaagccctg aaggacgtgg atccctgcta aatctctgat gttacattgc    60

<210> SEQ ID NO 35
<211> LENGTH: 681
<212> TYPE: DNA
<213> ORGANISM: Bacteriophage lambda

<400> SEQUENCE: 35
atgacaccgg acattatcct gcagcgtacc gggatcgatg tgagagctgt cgaacagggg     60
gatgatgcgt ggcacaaatt acggctcggc gtcatcaccg cttcagaagt tcacaacgtg    120
atagcaaaac cccgctccgg aaagaagtgg cctgacatga aaatgtccta cttccacacc    180
ctgcttgctg aggtttgcac cggtgtggct ccggaagtta cgctaaagc actggcctgg    240
ggaaaacagt acgagaacga cgccagaacc ctgtttgaat tcacttccgg cgtgaatgtt    300
actgaatccc cgatcatcta tcgcgacgaa agtatgcgta ccgcctgctc tcccgatggt    360
ttatgcagtg acggcaacgg ccttgaactg aaatgcccgt ttacctcccg ggatttcatg    420
aagttccggc tcggtggttt cgaggccata aagtcagctt acatggccca ggtgcagtac    480
agcatgtggg tgacgcgaaa aaatgcctgg tactttgcca actatgaccc gcgtatgaag    540
cgtgaaggcc tgcattatgt cgtgattgag cggatgaaa agtacatggc gagttttgac    600
gagatcgtgc cggagttcat cgaaaaaatg gacgaggcac tggctgaaat tggttttgta    660
tttggggagc aatggcgatg a                                              681

<210> SEQ ID NO 36

-continued

```
<211> LENGTH: 786
<212> TYPE: DNA
<213> ORGANISM: Bacteriophage lambda

<400> SEQUENCE: 36
atgagtactg cactcgcaac gctggctggg aagctggctg aacgtgtcgg catggattct      60
gtcgacccac aggaactgat caccactctt cgccagacgg catttaaagg tgatgccagc     120
gatgcgcagt tcatcgcatt actgatcgtt gccaaccagt acggccttaa tccgtggacg     180
aaagaaattt acgcctttcc tgataagcag aatggcatcg ttccggtggt gggcgttgat     240
ggctggtccc gcatcatcaa tgaaaaccag cagtttgatg gcatggactt tgagcaggac     300
aatgaatcct gtacatgccg gatttaccgc aaggaccgta atcatccgat ctgcgttacc     360
gaatggatgg atgaatgccg ccgcgaacca ttcaaaactc gcgaaggcag agaaatcacg     420
gggccgtggc agtcgcatcc caaacggatg ttacgtcata aagccatgat tcagtgtgcc     480
cgtctggcct tcggatttgc tggtatctat gacaaggatg aagccgagcg cattgtcgaa     540
aatactgcat acactgcaga acgtcagccg gaacgcgaca tcactccggt taacgatgaa     600
accatgcagg agattaacac tctgctgatc gccctggata aaacatggga tgacgactta     660
ttgccgctct gttcccagat atttcgccgc gacattcgtg catcgtcaga actgacacag     720
gccgaagcag taaaagctct tggattcctg aaacagaaag ccgcagagca gaaggtggca     780
gcatga                                                                786

<210> SEQ ID NO 37
<211> LENGTH: 417
<212> TYPE: DNA
<213> ORGANISM: Bacteriophage lambda

<400> SEQUENCE: 37
atggatatta atactgaaac tgagatcaag caaaagcatt cactaaccce ctttcctgtt      60 ttcctaatca gcccggcatt tcgcgggcga tattttcaca gctatttcag gagttcagcc     120
atgaacgctt attacattca ggatcgtctt gaggctcaga gctgggcgcg tcactaccag     180
cagctcgccc gtgaagagaa agaggcagaa ctggcagacg acatggaaaa aggcctgccc     240
cagcacctgt ttgaatcgct atgcatcgat catttgcaac gccacggggc cagcaaaaaa     300
tccattaccc gtgcgtttga tgacgatgtt gagtttcagg agcgcatggc agaacacatc     360
cggtacatgg ttgaaaccat tgctcaccac caggttgata ttgattcaga ggtataa       417
```